United States Patent
Green et al.

(10) Patent No.: US 10,485,680 B2
(45) Date of Patent: Nov. 26, 2019

(54) PROSTHETIC BLADE ATTACHMENT SYSTEM

(71) Applicant: NIKE, Inc., Beaverton, OR (US)

(72) Inventors: Jessica Green, Hillsboro, OR (US); Michelle Haines, Beaverton, OR (US); Monica Judge, Tigard, OR (US); Gerry Plasker, Beaverton, OR (US); Richard S. Ramsay, Portland, OR (US); Nicola J. Reynolds, Hillsboro, OR (US); Patrick D. Boyd, Aloha, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 15/474,536

(22) Filed: Mar. 30, 2017

(65) Prior Publication Data

US 2017/0281371 A1   Oct. 5, 2017

Related U.S. Application Data

(60) Provisional application No. 62/316,497, filed on Mar. 31, 2016.

(51) Int. Cl.
*A61F 2/66* (2006.01)
*A61F 2/76* (2006.01)
*A61F 2/50* (2006.01)

(52) U.S. Cl.
CPC ............... *A61F 2/66* (2013.01); *A61F 2/76* (2013.01); *A61F 2002/5003* (2013.01);
(Continued)

(58) Field of Classification Search
CPC ...... A61F 2/66; A61F 2/76; A61F 2/78; A61F 2002/5001; A61F 2002/5083;
(Continued)

(56) References Cited

U.S. PATENT DOCUMENTS 5,692,322 A * 12/1997 Lombardino ............ A43B 3/24
36/100
8,535,390 B1 * 9/2013 Lecomte .................. A61F 2/66
623/53
(Continued)

FOREIGN PATENT DOCUMENTS

GB           978586 A      12/1964
WO     WO-9840038 A1      9/1998
(Continued)

OTHER PUBLICATIONS

International Searching Authority (EPO), International Search Report and Written Opinion for Application No. PCT/US2017/025238, dated Sep. 13, 2017.
(Continued)

*Primary Examiner* — Thomas Sweet
*Assistant Examiner* — Christie L Bahena
(74) *Attorney, Agent, or Firm* — Honigman LLP; Matthew H. Szalach; Jonathan P. O'Brien

(57) ABSTRACT

An attachment system for use with a prosthetic device includes a first component including a first surface, and further including one of a channel and a projection disposed on an opposite side of the first component than the first surface. A second component including a second surface, and including the other of the channel and the projection disposed on an opposite side of the second component than the second surface, the other slidably engaging the channel or the projection to selectively couple the first component and the second component together. One of the first surface and the second surface is operable to be attached to the prosthetic device, and the other is operable to be attached to a sole structure having a ground-engaging surface.

17 Claims, 16 Drawing Sheets

(52) U.S. Cl.
CPC ......... *A61F 2002/5072* (2013.01); *A61F 2002/5083* (2013.01); *A61F 2002/665* (2013.01); *A61F 2002/6614* (2013.01); *A61F 2002/6671* (2013.01)

(58) Field of Classification Search
CPC ...... A61F 2002/6614; A61F 2002/6621; A61F 2002/6628; A61F 2002/6635; A61F 2002/6642; A61F 2002/665
See application file for complete search history.

(56) References Cited

U.S. PATENT DOCUMENTS

| | | | | |
|---|---|---|---|---|
| 2006/0041321 | A1* | 2/2006 | Christensen | A61F 2/6607 623/38 |
| 2014/0276500 | A1* | 9/2014 | Scott | A61F 5/449 604/343 |
| 2016/0331558 | A1* | 11/2016 | Kampas | A61F 2/50 |

FOREIGN PATENT DOCUMENTS

| | | |
|---|---|---|
| WO | WO-9918895 A1 | 4/1999 |
| WO | WO-2005041819 A2 | 5/2005 |

OTHER PUBLICATIONS

International Searching Authority (EPO), International Preliminary Report on Patentability for Application No. PCT/US2017/025238, dated Oct. 11, 2018.

* cited by examiner

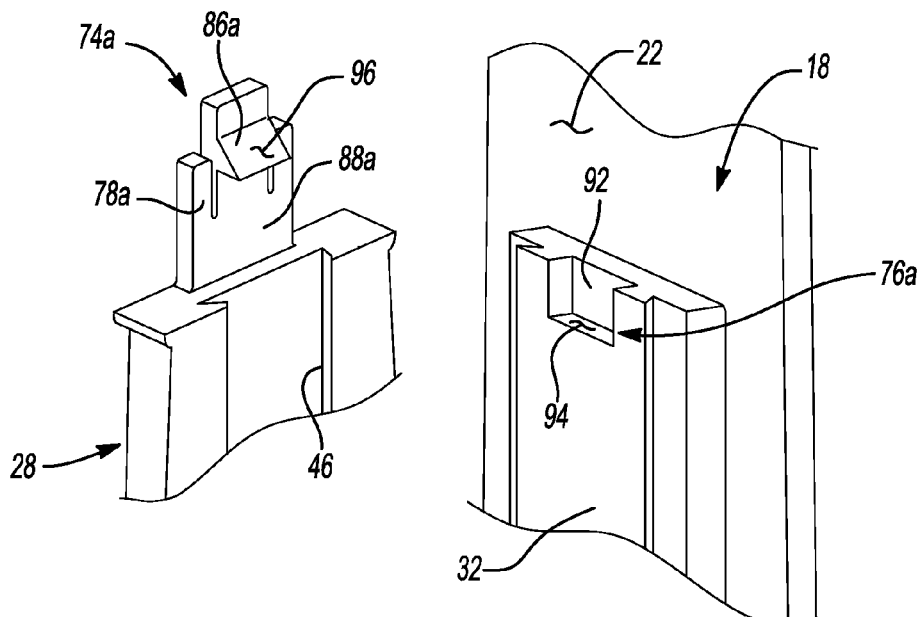
Fig-6A
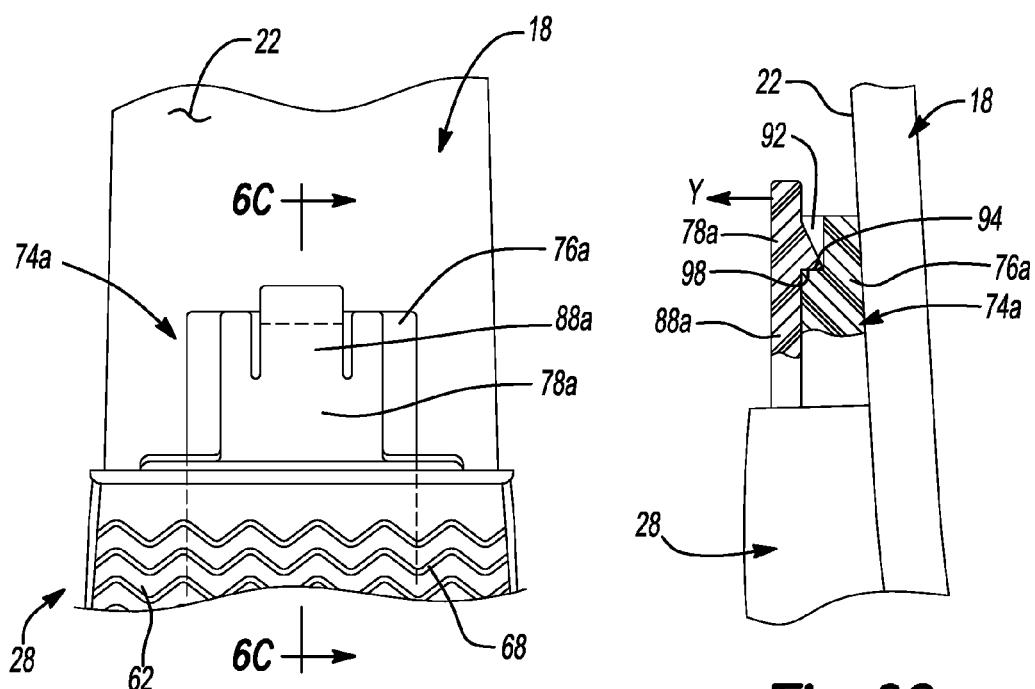
Fig-6B
Fig-6C

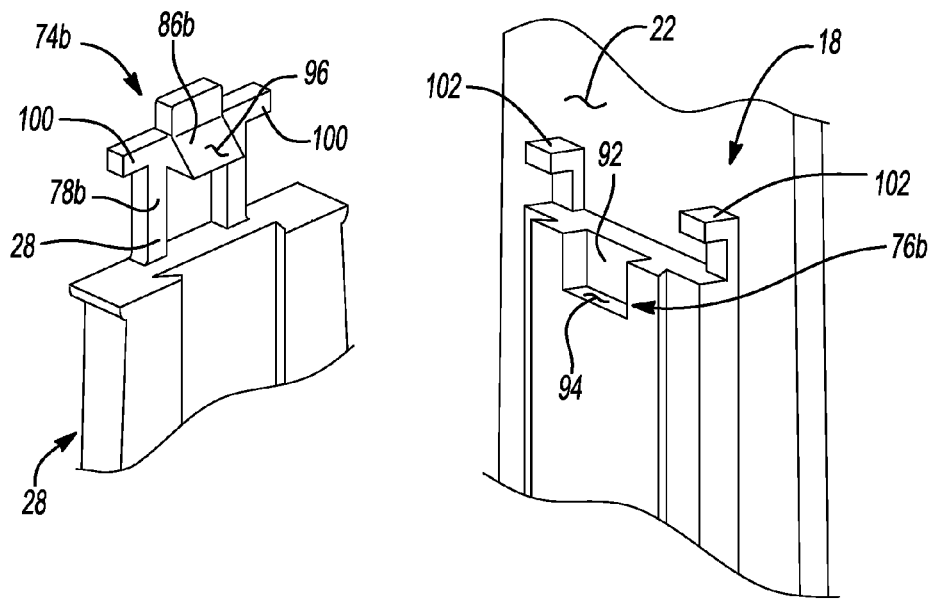
*Fig-7A*
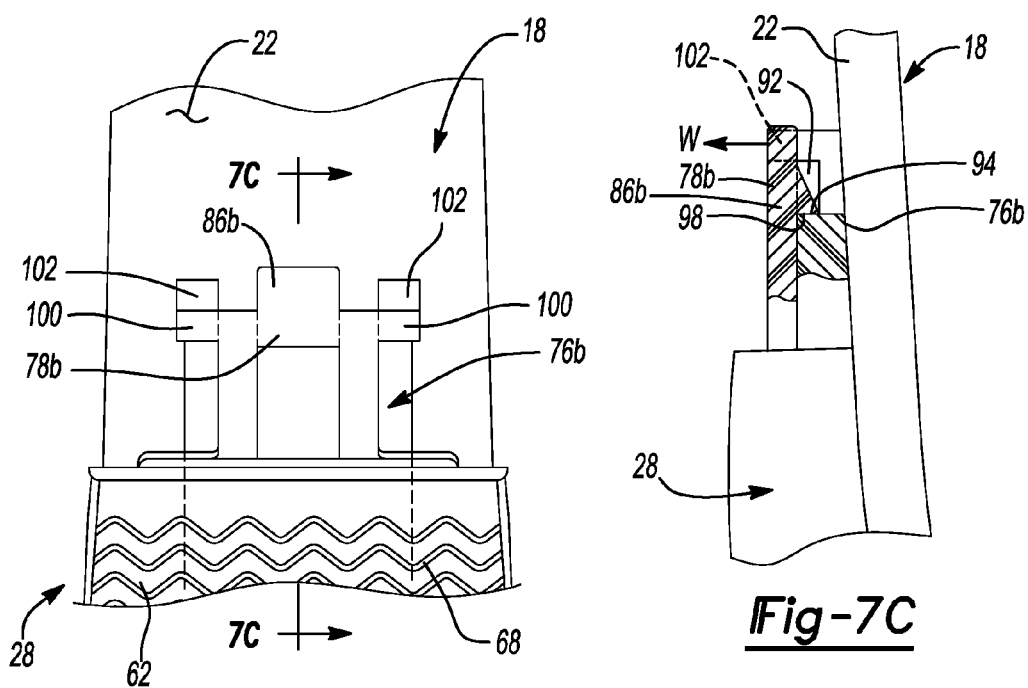
*Fig-7B*
*Fig-7C*

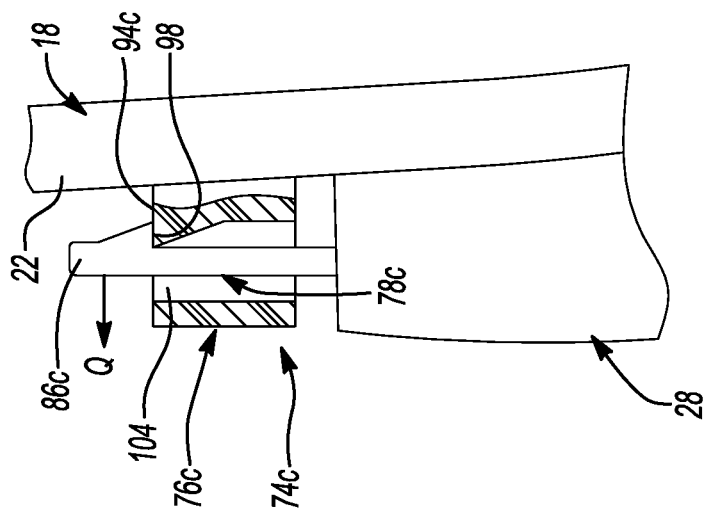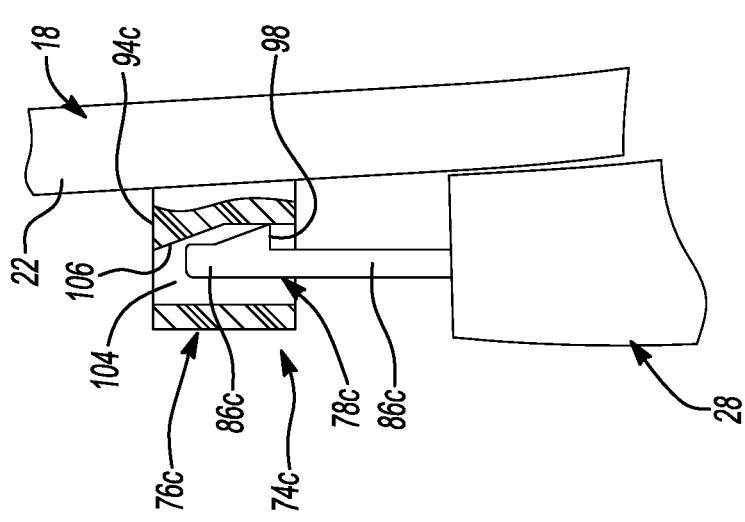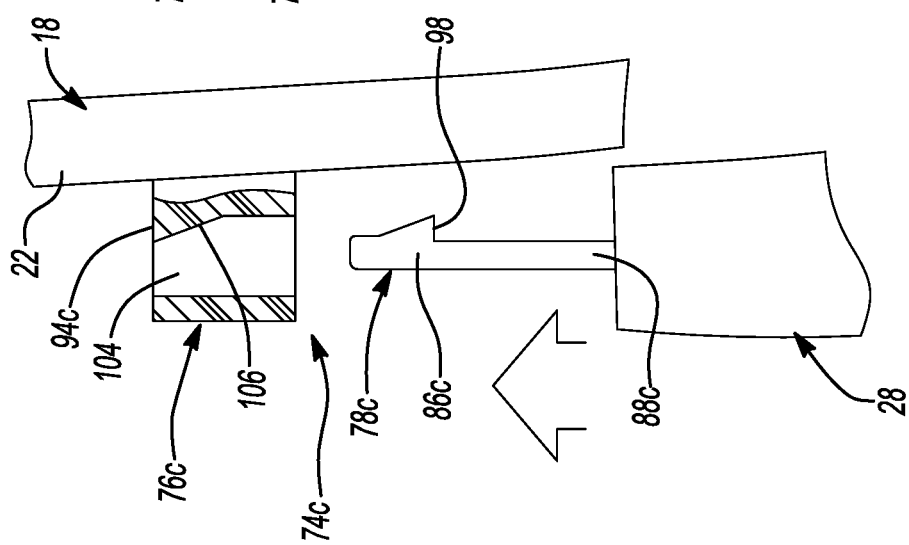

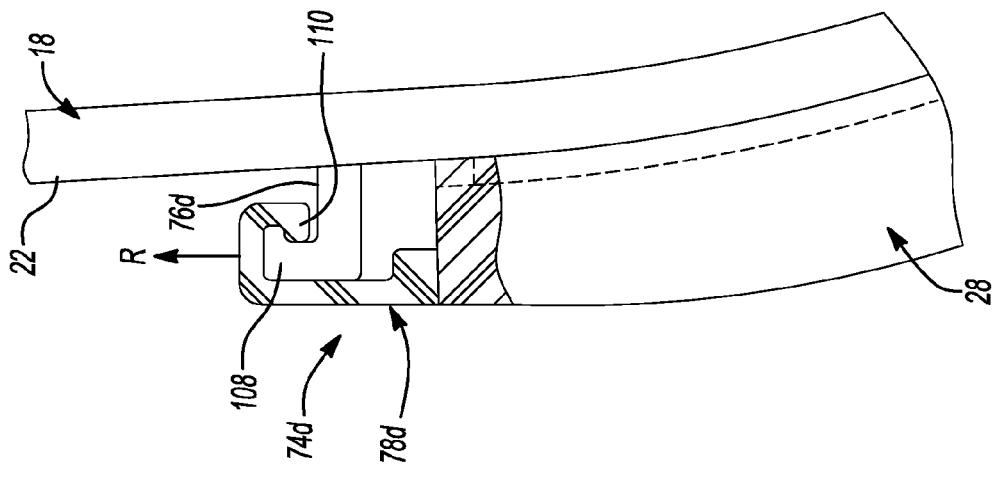
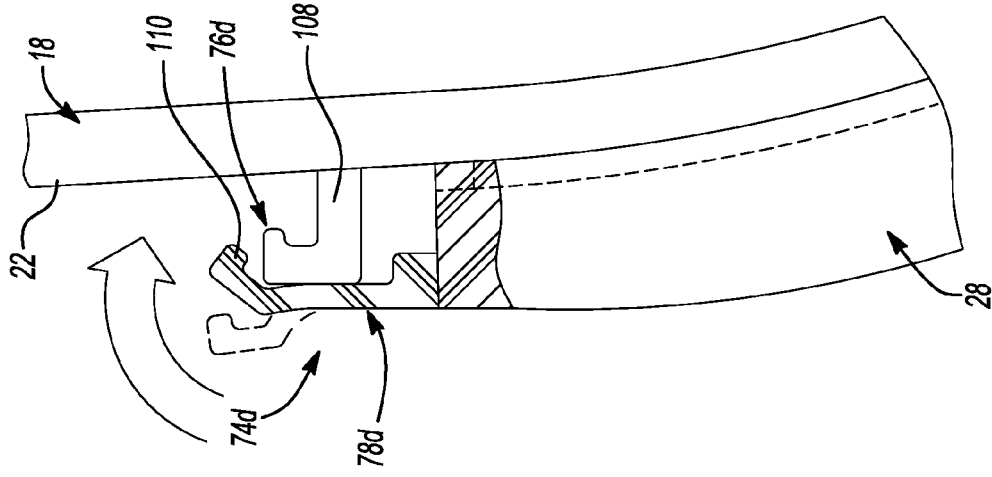
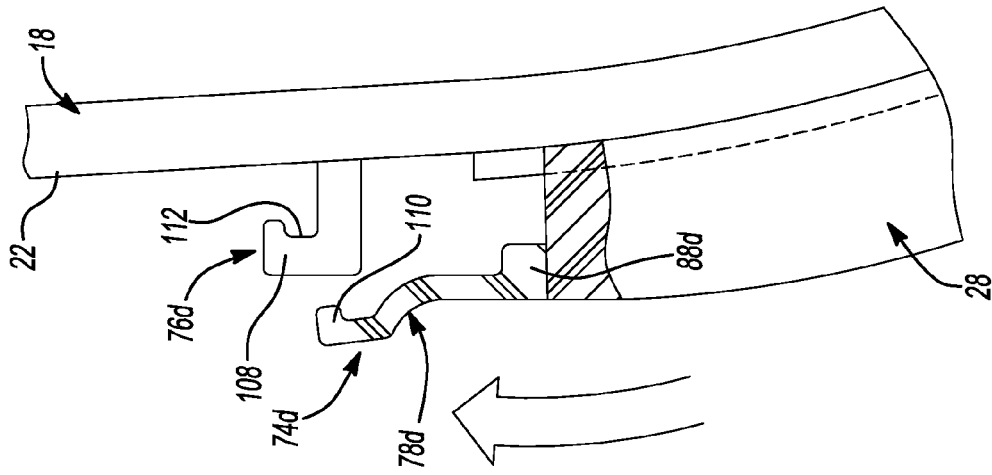

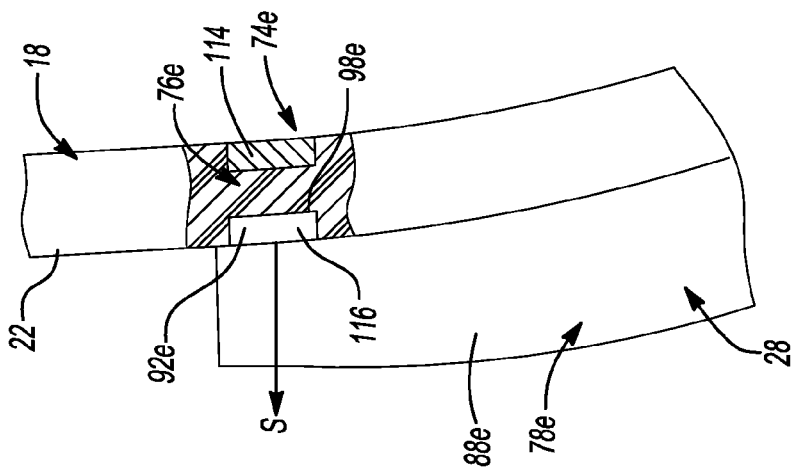
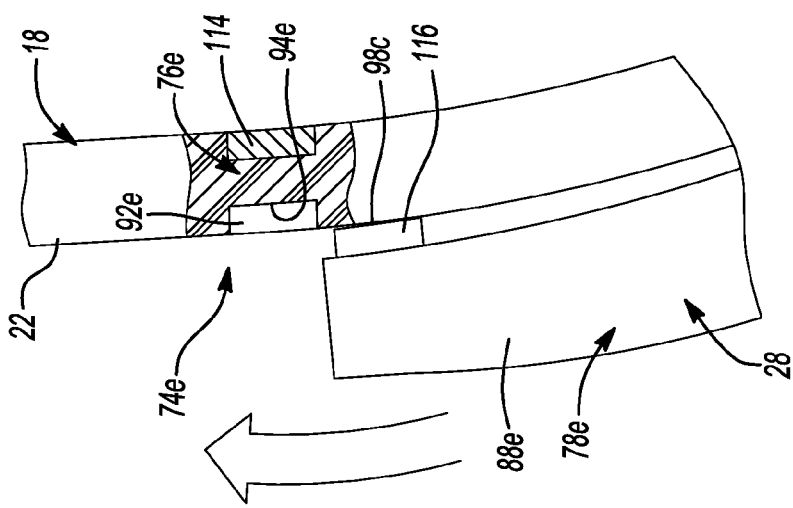
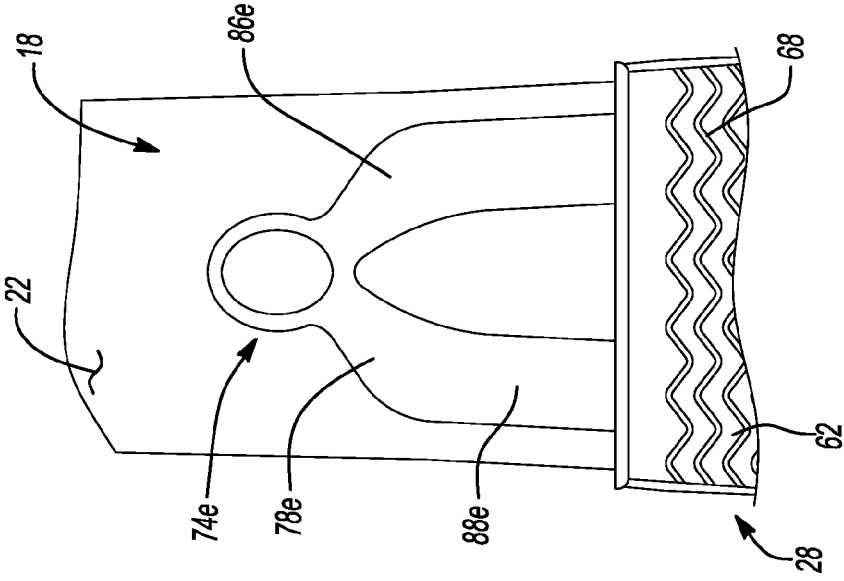
Fig-10C
Fig-10B
Fig-10A

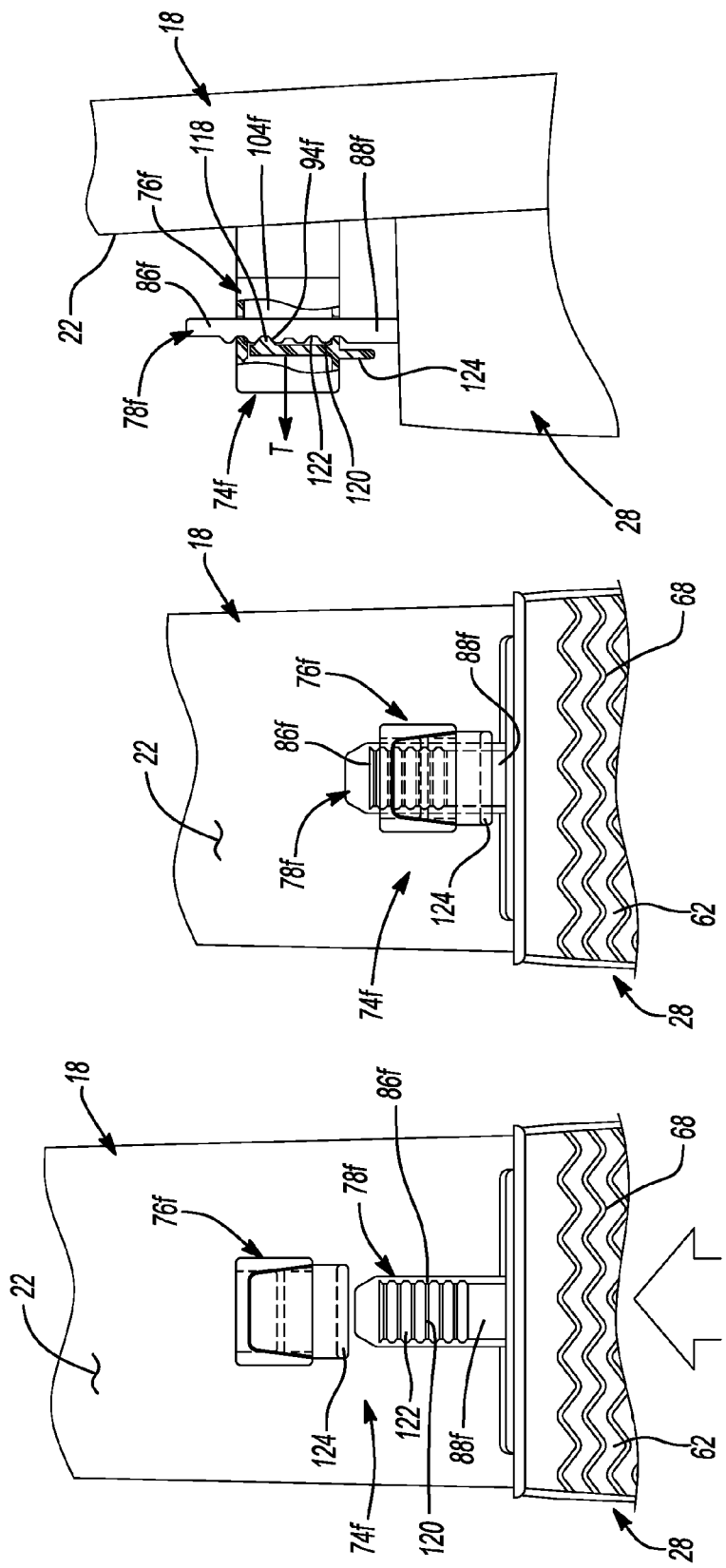

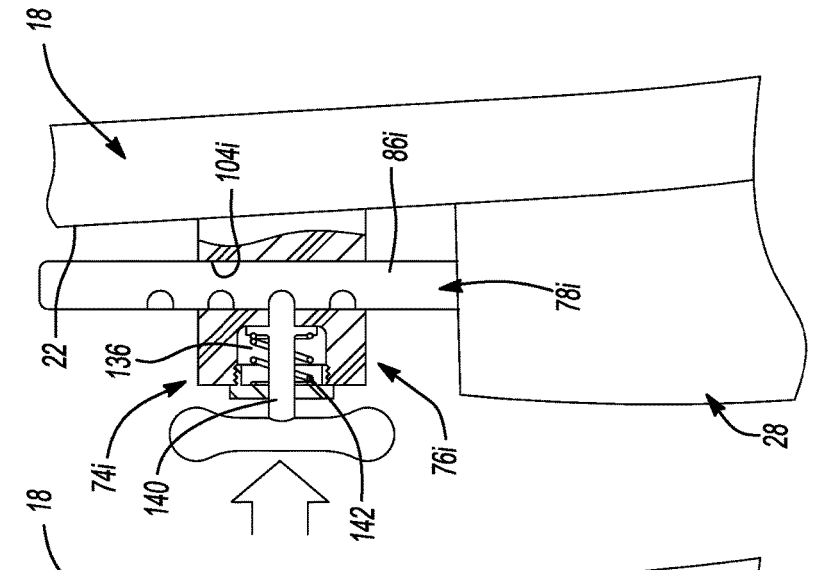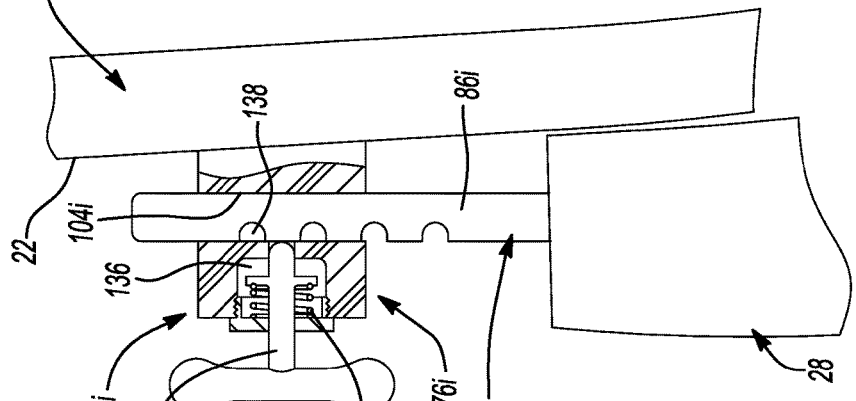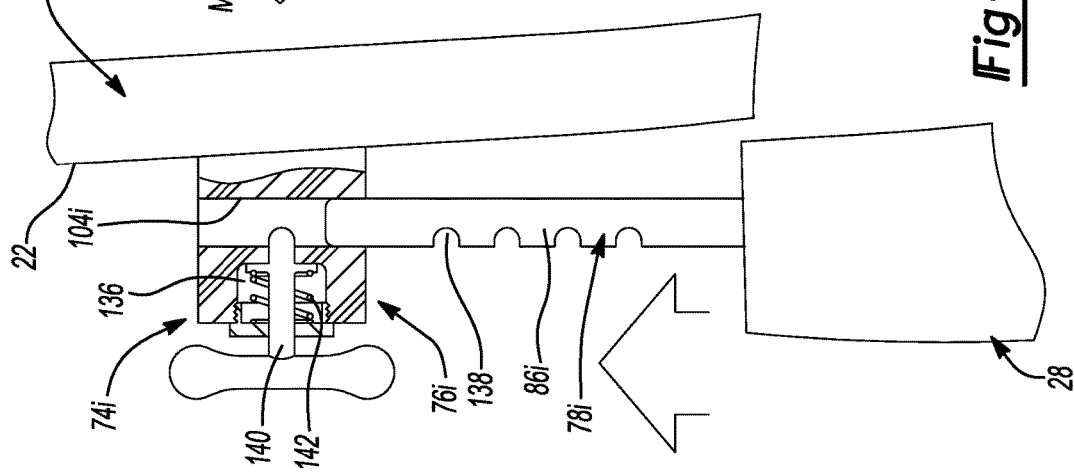

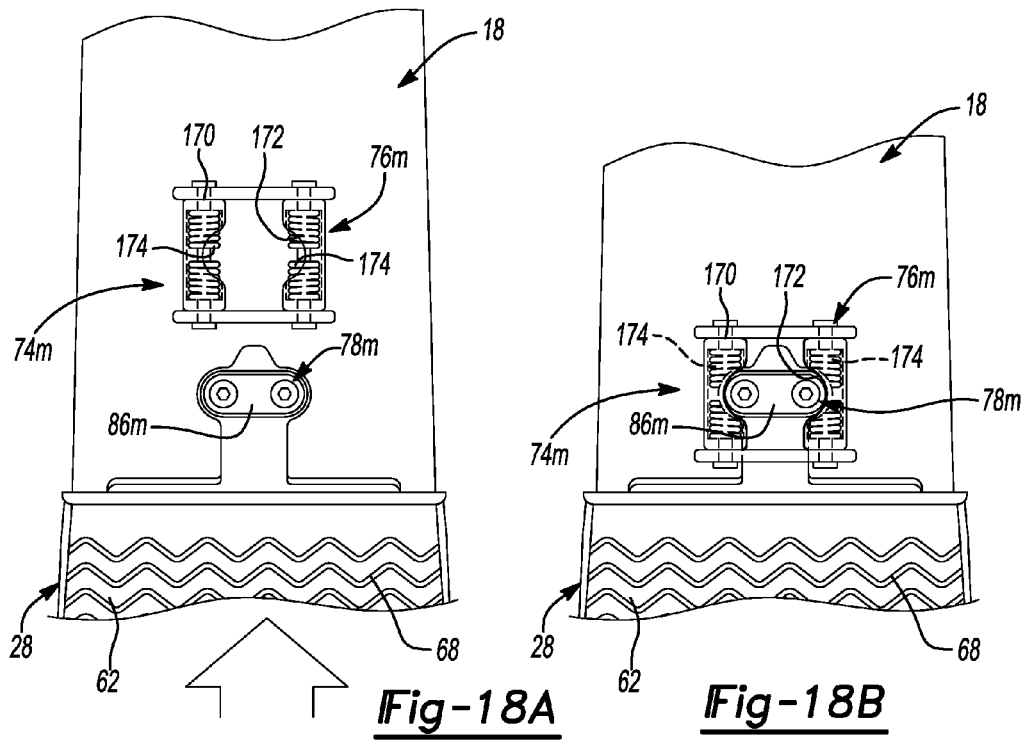
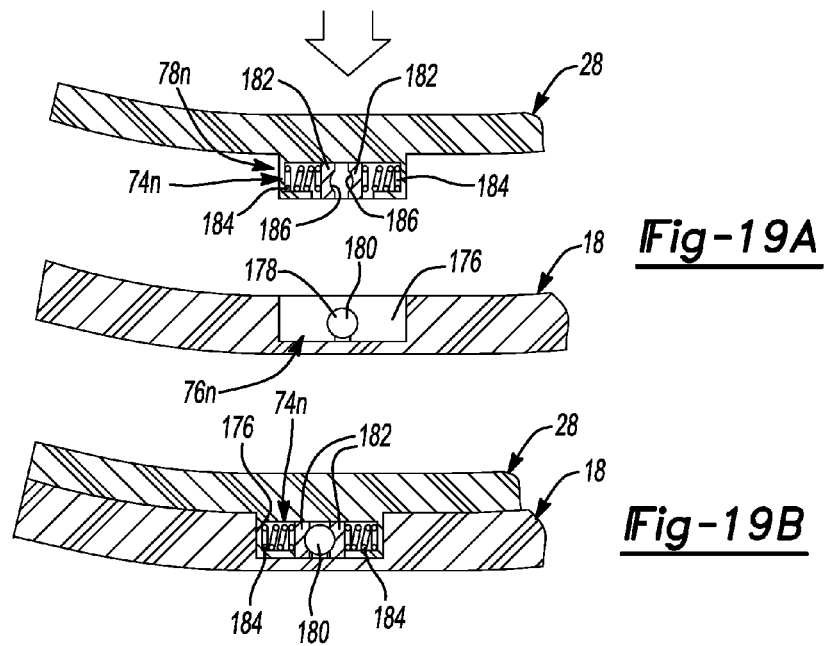

PROSTHETIC BLADE ATTACHMENT SYSTEM

CROSS REFERENCE TO RELATED APPLICATION

This application claims priority to U.S. Provisional Application Ser. No. 62/316,497, filed Mar. 31, 2016, the disclosure of which is hereby incorporated by reference in its entirety.

FIELD

The present disclosure relates to attachment systems and more particularly to an attachment system for securing to a prosthetic device a component having a ground-contacting surface.

BACKGROUND

This section provides background information related to the present disclosure and is not necessarily prior art.

Prosthetic devices are used by amputees to replace all of, or some portion of, a limb. For example, prosthetic legs may be used to replace a portion of a person's leg surgically removed at or above the knee. Such prosthetic devices allow the person to walk in a conventional manner by supporting the person's weight and, in some cases, by providing a prosthetic joint at the person's knee that bends and otherwise mimics operation of a human knee. Prosthetic legs may be incorporated at one or both of the person's legs depending on the person's condition.

Prosthetic legs may be used in conjunction with prosthetic feet that are designed to replace the foot of the amputee. As with prosthetic legs, prosthetic feet are designed to allow an amputee to walk in a conventional manner by supporting the person's weight during use. Prosthetic feet are sometimes also designed to flex and bend in an effort to function in a similar manner as a human ankle and foot.

One conventional prosthetic foot is a so-called prosthetic blade that includes a substantially flat member extending from a distal end of a prosthetic leg. Prosthetic blades are typically formed from a resilient material that permits the blade to bend and flex during use while automatically returning to a relaxed state once an applied force is released. Such bending and flexing of the prosthetic blade is enhanced by the generally curved shape of the blade that facilitates bending and flexing when the blade comes in contact with the ground during use. The foregoing properties of prosthetic blades allow the blades to absorb energy associated with ground-contacting forces and, as such, provide an amputee with a degree of comfort during use. Further, such bending and flexing provides the amputee with an energy return during walking and running movements that enhances the performance of the amputee during such movements.

While prosthetic blades provide an amputee with the ability to walk and run, such blades do not typically include a ground-contacting surface suitable for all potential activities. Accordingly, prosthetic blades may be fitted with an outsole that is affixed to the blade using an adhesive to restrict relative movement between the material of the blade and the material of the outsole. While such outsoles protect the blade during use and, further, enhance the traction of the blade with the ground during some uses, such outsoles are difficult to attach and, further, are even more difficult to remove. Accordingly, the few outsoles currently used in conjunction with prosthetic blades cannot be easily interchanged with one another for use in a particular activity or with a particular ground surface.

DRAWINGS

The drawings described herein are for illustrative purposes only of selected configurations and not all possible implementations, and are not intended to limit the scope of the present disclosure.

Figure 1:
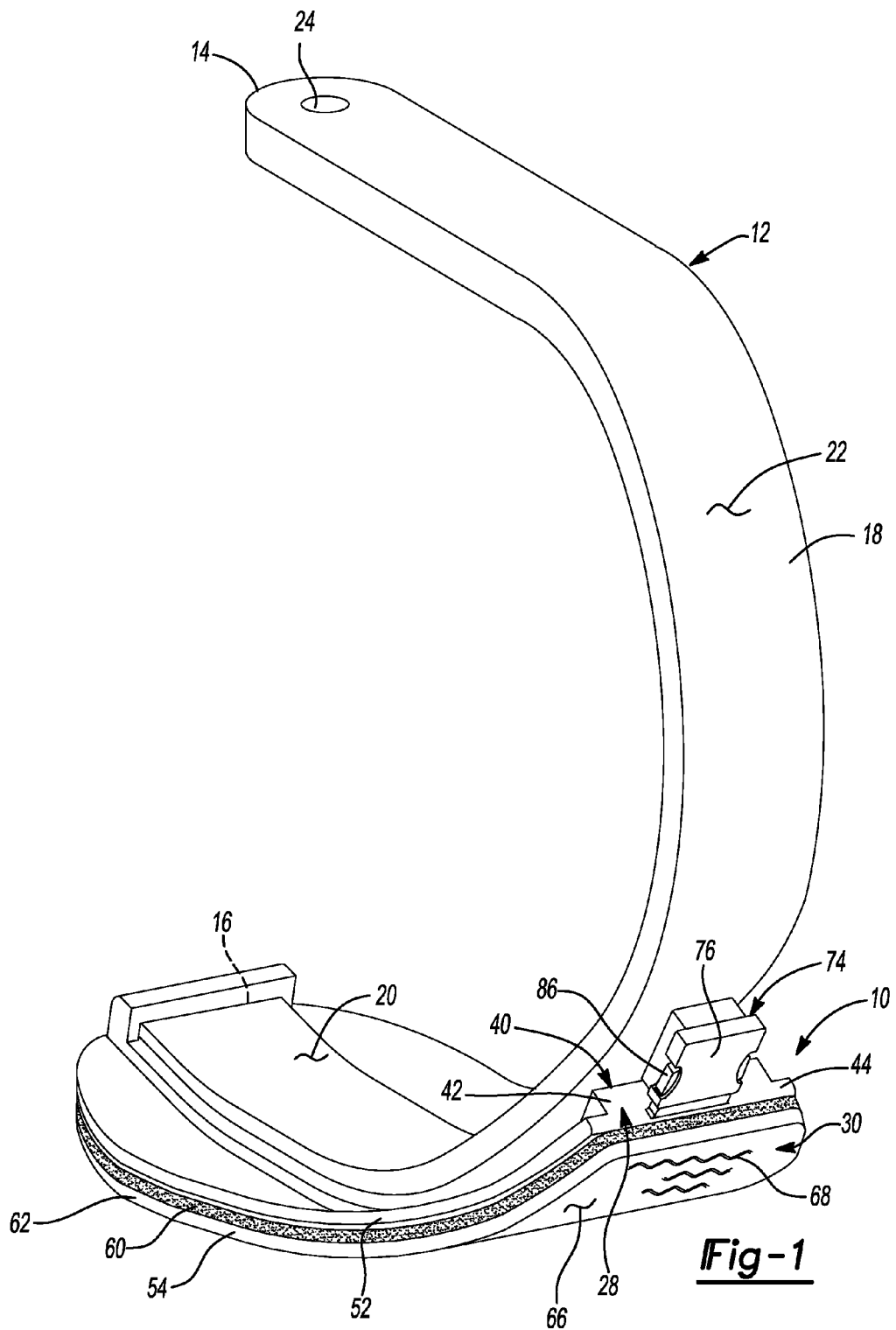
FIG. 1 is a perspective view of a prosthetic device.
Figures 12A, 12B:
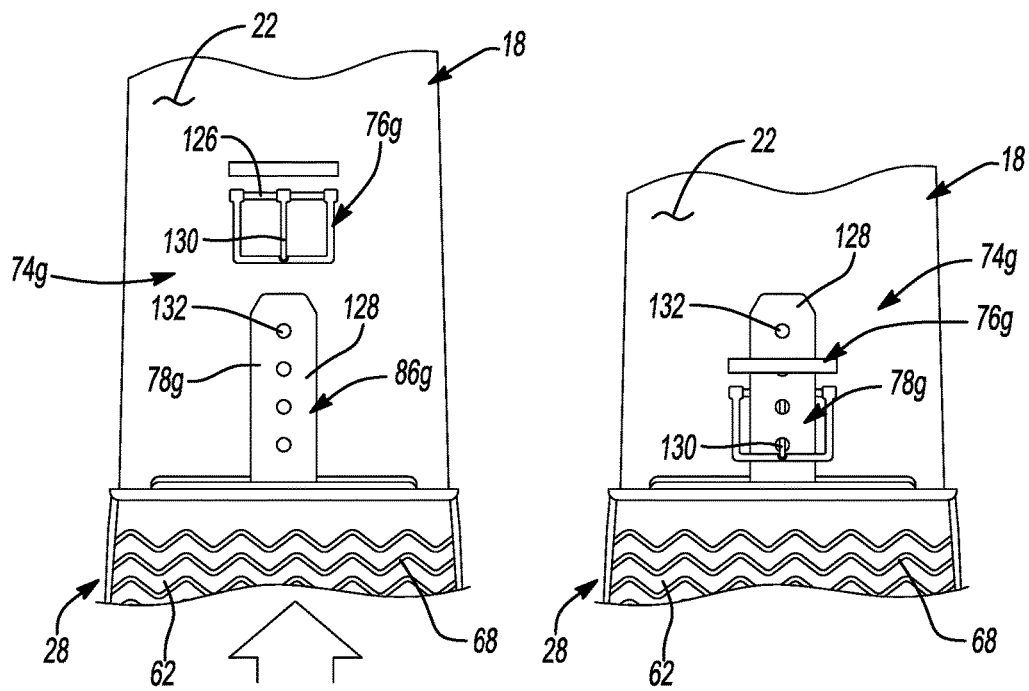
Figures 13A, 13B:
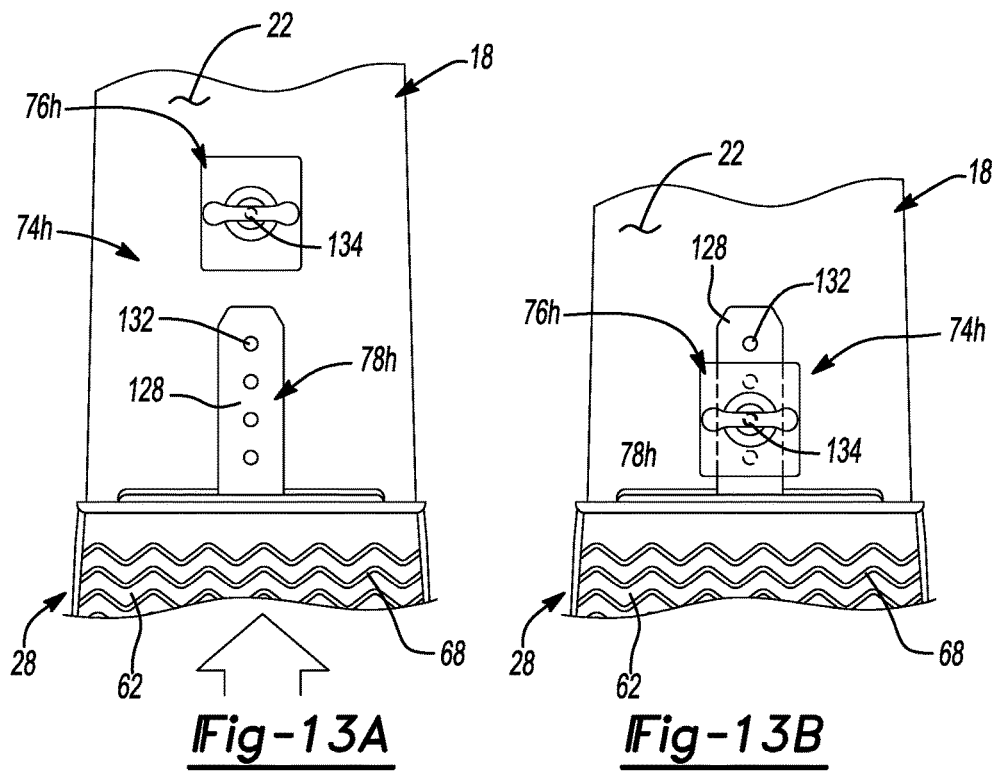
Figures 15A, 15B, 15C:
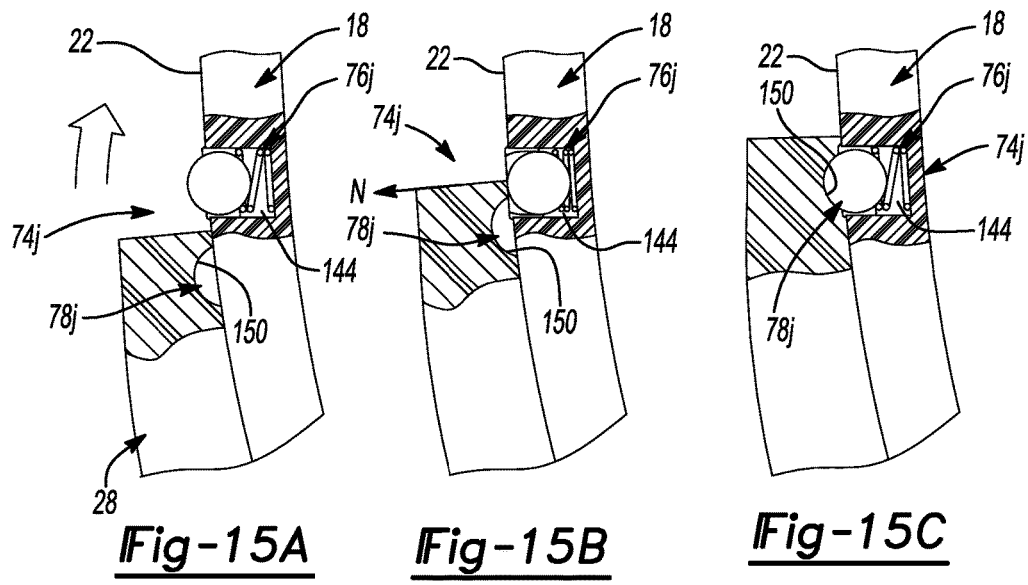
Figures 16A, 16B:
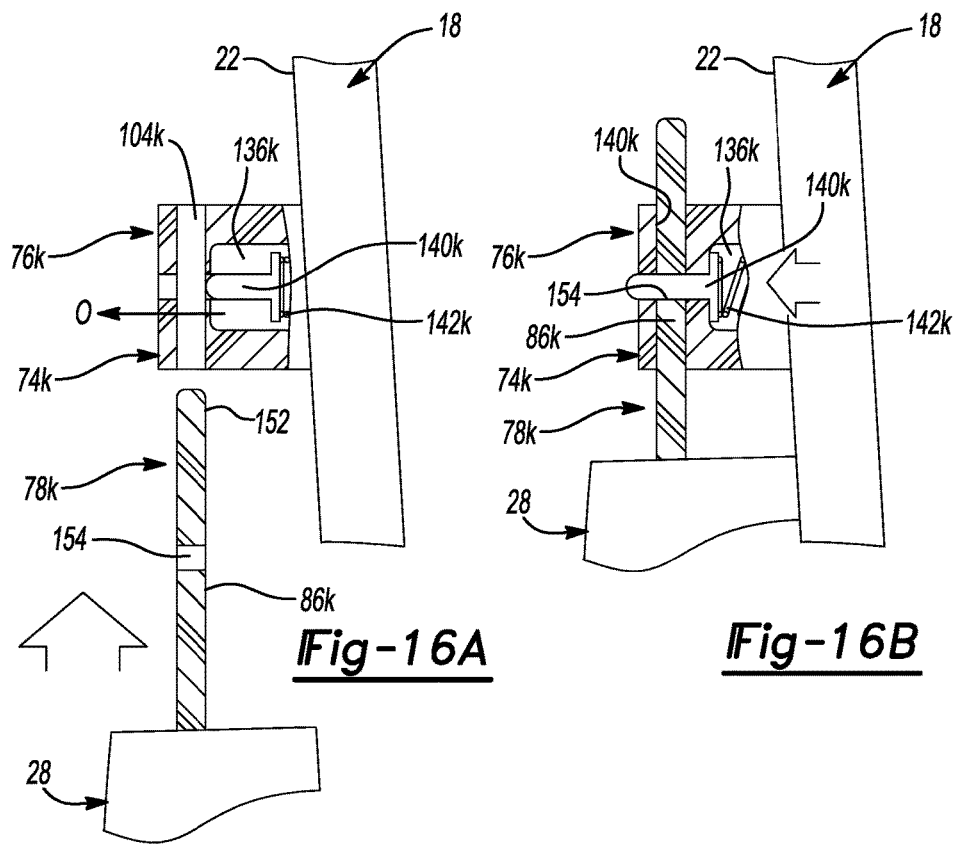
Figure 17A:
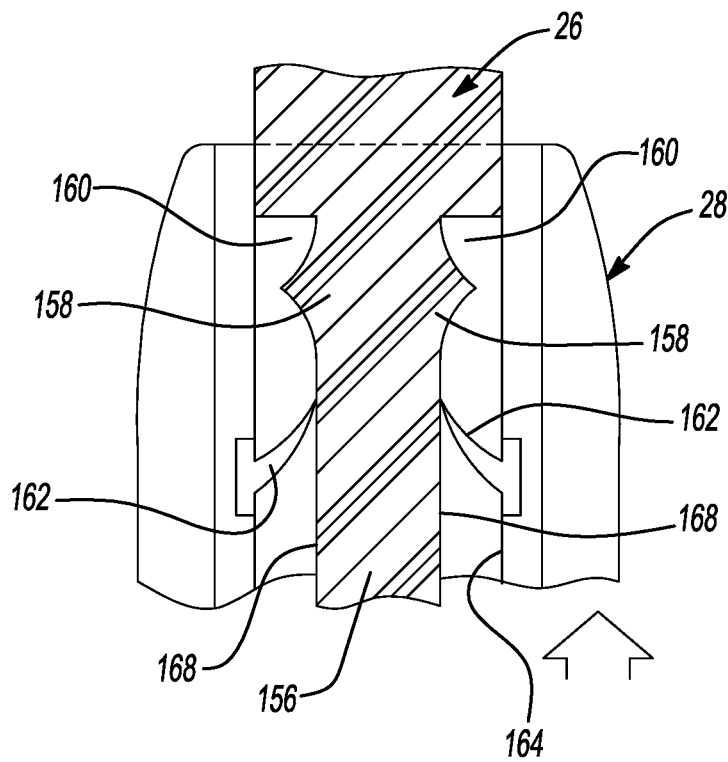
Figure 17B:
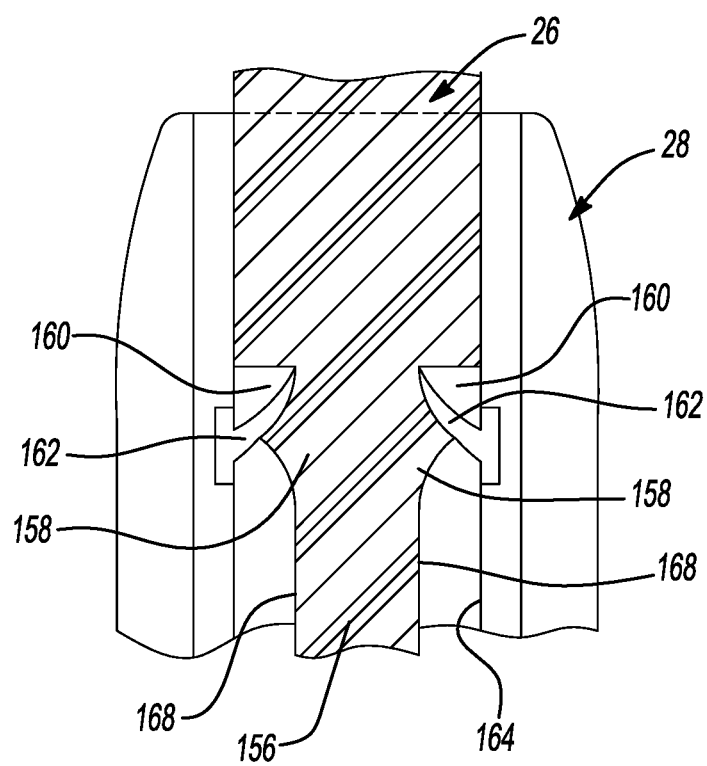

FIG. 6A a partial exploded perspective view of a latch mechanism for use with the prosthetic device of FIG. 1 shown in an unlatched state;

FIG. 6B is a top view of the latch mechanism of FIG. 6A shown in a latched state;

FIG. 6C is a partial cross-sectional view of the latch mechanism of FIG. 6A taken along line 6C-6C of FIG. 6B and shown in a latched state;

FIG. 7A a partial exploded perspective view of a latch mechanism for use with the prosthetic device of FIG. 1 shown in an unlatched state;

FIG. 7B is a top view of the latch mechanism of FIG. 7A shown in a latched state;

FIG. 7C is a partial cross-sectional view of the latch mechanism of FIG. 7A taken along line 7C-7C of FIG. 7B and shown in a latched state;

FIG. 8A is a partial cross-sectional view of a latch mechanism for use with the prosthetic device of FIG. 1 shown in an unlatched state;

FIG. 8B is a partial cross-sectional view of the latch mechanism of FIG. 8A moving from an unlatched state toward a latched state;

FIG. 8C is a partial cross-sectional view of the latch mechanism of FIG. 8A shown in a latched state;

FIG. 9A is a partial cross-sectional view of a latch mechanism for use with the prosthetic device of FIG. 1 shown in an unlatched state;

FIG. 9B is a partial cross-sectional view of the latch mechanism of FIG. 9A moving from an unlatched state toward a latched state;

FIG. 9C is a partial cross-sectional view of the latch mechanism of FIG. 9A shown in a latched state;

FIG. 10A is a top view of a latch mechanism for use with the prosthetic device of FIG. 1;

FIG. 10B is a partial cross-sectional view of the latch mechanism of FIG. 10A moving from an unlatched state toward a latched state;

FIG. 10C is a partial cross-sectional view of the latch mechanism of FIG. 10A in a latched state;

FIG. 11A a top view of a latch mechanism for use with the prosthetic device of FIG. 1 shown in an unlatched state;

FIG. 11B is a top view of the latch mechanism of FIG. 11B shown in a latched state;

FIG. 11C is a partial cross-sectional view of the latch mechanism of FIG. 11A taken along line 11C-11C of FIG. 11B and shown in the latched state;

FIG. 12A is a top view of a latch mechanism for use with the prosthetic device of FIG. 1 shown in an unlatched state;

FIG. 12B is a top view of the latch mechanism of FIG. 12A shown in a latched state;

FIG. 13A is a top view of a latch mechanism for use with the prosthetic device of FIG. 1 shown in an unlatched state;

FIG. 13B is a top view of the latch mechanism of FIG. 13A shown in a latched state;

FIG. 14A is a partial cross-sectional view of a latch mechanism for use with the prosthetic device of FIG. 1 shown in an unlatched state;

FIG. 14B is a partial cross-sectional view of the latch mechanism of FIG. 14A moving from an unlatched state toward a latched state;

FIG. 14C is a partial cross-sectional view of the latch mechanism of FIG. 14A shown in a latched state;

FIG. 15A is a partial cross-sectional view of a latch mechanism for use with the prosthetic device of FIG. 1 shown in an unlatched state;

FIG. 15B is a partial cross-sectional view of the latch mechanism of FIG. 15A moving from an unlatched state toward a latched state;

FIG. 15C is a partial cross-sectional view of the latch mechanism of FIG. 15A shown in a latched state;

FIG. 16A is a partial cross-sectional view of a latch mechanism for use with the prosthetic device of FIG. 1 shown in an unlatched state;

FIG. 16B is a partial cross-sectional view of the latch mechanism of FIG. 16A shown in a latched state;

FIG. 17A is a top view of a latch mechanism for use with the prosthetic device of FIG. 1 shown in an unlatched state;

FIG. 17B is a top view of the latch mechanism of FIG. 17A shown in a latched state;

FIG. 18A is a top view of a latch mechanism for use with the prosthetic device of FIG. 1 shown in an unlatched state;

FIG. 18B is a top view of the latch mechanism of FIG. 18A shown in a latched state;

FIG. 19A is a partial cross-sectional view of a latch mechanism for use with the prosthetic device of FIG. 1 shown in an unlatched state; and FIG. 19B is a partial cross-sectional view of the latch mechanism of FIG. 19A shown in a latched state.

Corresponding reference numerals indicate corresponding parts throughout the drawings.

DETAILED DESCRIPTION

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

When an element or layer is referred to as being "on," "engaged to," "connected to," "attached to," or "coupled to" another element or layer, it may be directly on, engaged, connected, attached, or coupled to the other element or layer, or intervening elements or layers may be present. In contrast, when an element is referred to as being "directly on," "directly engaged to," "directly connected to," "directly attached to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terms first, second, third, etc. may be used herein to describe various elements, components, regions, layers and/or sections. These elements, components, regions, layers and/or sections should not be limited by these terms. These terms may be only used to distinguish one element, component, region, layer or section from another region, layer or section. Terms such as "first," "second," and other numerical terms do not imply a sequence or order unless clearly indicated by the context. Thus, a first element, component, region, layer or section discussed below could be termed a second element, component, region, layer or section without departing from the teachings of the example configurations.

An attachment system for use with a prosthetic device is provided. The attachment system includes a first component including a first surface, and further including one of a channel and a projection disposed on an opposite side of the first component than the first surface. The system also includes a second component including a second surface, and further including the other of the channel and the projection disposed on an opposite side of the second component than the second surface, the other of the channel and the projection slidably engaging the one of the channel and the projection to selectively couple the first component and the second component together. One of the first surface and the second surface is operable to be attached to the prosthetic device, and the other of the first surface and the second surface is operable to be attached to a sole structure having a ground-engaging surface.

Implementations of the disclosure may include one or more of the following optional features. In some implementations, the channel matingly receives the projection therein. The projection may include a first portion that is disposed at a junction of the prosthetic device and the one of the first surface and the second surface and a second portion that is spaced apart from the first portion and is received by the channel, whereby the projection has a cross-section that is wider at the second portion than at the first portion to restrict removal of the projection from the channel. The channel and the projection may cooperate to selectively provide a dovetail connection between the first component and the second component.

The sole structure may include a cushioning layer disposed between the other of the first surface and the second surface and the ground-engaging surface. In some examples, the ground-engaging surface is formed by the cushioning layer. The ground-engaging surface may be formed by an outsole layer that is attached to the cushioning layer.

In some implementations, the attachment system includes a latch mechanism operable to fix a relative position between the first component and the second component. The latch mechanism may be automatically moved into a latched state to fix the relative position between the first component and the second component when the projection is moved into the channel a predetermined distance. The latch mechanism may include a male component that is fixed for movement with one of the first component and the second component and a female component that is fixed for movement with the other of the first component and the second component, the female component receiving the male component and securing the male component to the female component when the projection is moved the predetermined distance into the channel. The latch mechanism may also include a latching element fixed for movement with one of the first component and the second component, and further includes a latching feature fixed for movement with the other of the first component and the second component, the latching element operable to be actuated by and to engage the latching feature in response to a sliding engagement between the first component and the second component. The other of the first component and the second component may include a ramping surface operable to deflect the latching element and to position the latching element into engagement with the latching feature in response to the one of the first component and the second component slidingly engaging with the other of the first component and the second component.

In some examples, the prosthetic device is a foot prosthetic device or the prosthetic device may be a blade prosthetic device. The first component and the second component may be elongated components.

Another aspect of the disclosure provides an attachment system for use with a prosthetic device. The attachment includes a first elongate component attached to the prosthetic device and a second elongate component attached to a sole structure having a ground-engaging surface. The second elongate component slidably engages the first elongate component to attach the sole structure to the prosthetic device.

This aspect may include one or more of the following optional features. In some implementations, the second elongate component matingly receives the first elongate component therein. The first elongate component may include a projection extending from a surface of the prosthetic device. The projection may include a first portion disposed at a junction of the projection and the surface of the prosthetic device and a second portion that is spaced apart from the first portion and is received by a channel. A cross-section of the projection may be wider at the second portion than at the first portion. The channel and the projection may cooperate to selectively provide a dovetail connection between the first elongate component and the second elongate component. In some examples, the sole structure includes a cushioning layer disposed between the second elongate component and the ground-engaging surface. The ground-engaging surface may be formed by the cushioning layer. The ground-engaging surface may be formed by an outsole layer that is attached to the cushioning layer.

In some implementations, the attachment system includes a latch mechanism operable to selectively fix a relative position between the first elongate component and the second elongate component. The latch mechanism may be automatically moved into a latched state to fix the relative position between the first elongate component and the second elongate component when the first elongate component is moved into the second elongate component a predetermined distance. The latch mechanism may include a male component that is fixed for movement with one of the first elongate component and the second elongate component, and further includes a female component that is fixed for movement with the other of the first elongate component and the second elongate component. The female component may receive the male component and secure the male component to the female component when the first elongate component is moved the predetermined distance into the second elongate component. In some examples, the latch mechanism includes a latching element fixed for movement with one of the first elongate component and the second elongate component, and a latching feature fixed for movement with the other of the first elongate component and the second elongate component. The latching element may be operable to be moved relative to the one of the first elongate component and the second elongate component to engage the latching feature.

In some examples, the other of the first elongate component and the second elongate component includes a ramping surface operable to deflect the latching element and to position the latching element into engagement with the latching feature. The prosthetic device may be a foot prosthetic device. The prosthetic device may be a blade prosthetic device, in some examples. The first elongate component may be integrally formed with the prosthetic device.

Yet another aspect of the disclosure provides an attachment system for a prosthetic device. The attachment system includes a first component attached to the prosthetic device and including a first latch mechanism, and a second component selectively attachable to the first component. The second component includes a second latch mechanism and a ground-engaging surface. The second latch mechanism is configured and disposed to latchingly engage with the first latch mechanism when the first component is moved a predetermined distance relative to the second component in a first direction.

This aspect may include one or more of the following optional features. In some implementations, the second latch mechanism is disposed on an opposite side of the second component than the ground-engaging surface. The second component may be slidably attached to the first component. The first component may include one of a projection and a channel and the second component includes the other of the projection and the channel. The channel may receive the projection to guide movement of the first component relative to the second component.

In some examples, the projection is matingly received by the channel and is permitted to slide relative to and within the channel to permit movement of the first component relative to the second component in the first direction. The projection may include a first end that is attached to one of the first component and the second component and a second end that is spaced apart from the first end and is received by the channel of the other of the first component and the second component. The projection may have a cross-section that increases in width from the first end to the second end to restrict removal of the projection from the channel. A second portion may include a cushioning layer disposed between the prosthetic device and the ground-engaging surface. In some examples, the ground-engaging surface is formed by the cushioning layer. The ground-engaging surface may be formed by an outsole layer that is attached to the cushioning layer.

In some examples, the first latch mechanism includes one of a male component and a female component that is fixed for movement with the first component. The second latch mechanism may include the other of the male component and the female component, the female component being fixed for movement with the second component and may receive the male component to secure the male component to the female component when the first component is moved the predetermined distance in the first direction.

Yet another aspect of the disclosure provides an attachment system for a prosthetic device. The attachment system includes a first component fixed for movement with the prosthetic device and a second component that matingly receives the first component and includes a ground-engaging surface. The second component is automatically secured to the first component when the first component is moved a predetermined distance relative to the second component in a first direction.

This aspect may include one or more of the following optional features. In some implementations, the first component includes a first latch mechanism and the second component includes a second latch mechanism. The second latch mechanism may engage the first latch mechanism when the first component is moved the predetermined distance relative to the second component in the first direction. The first latch mechanism may include one of a male component and a female component that is fixed for movement with the first component and the second latch mechanism includes the other of the male component and the female component. The female component may be fixed for movement with the second component and may receive the male component to secure the male component to the female component when the first component is moved the predetermined distance in the first direction. The second latch mechanism may be disposed on an opposite side of the second component than the ground-engaging surface. The second component may be slidably attached to the first component. In some examples, the first component includes one of a projection and a channel and the second component includes the other of the projection and the channel. The channel may receive the projection to guide movement of the first component relative to the second component.

In some implementations, the projection is matingly received by the channel and is permitted to slide relative to and within the channel to permit movement of the first component relative to the second component in the first direction. The projection may include a first end that is attached to one of the first component and the second component and a second end that is spaced apart from the first end and is received by the channel of the other of the first component and the second component. The projection may have a cross-section that increases in width from the first end to the second end to restrict removal of the projection from the channel. In some examples, the second component includes a cushioning layer, the cushioning layer being disposed between the prosthetic device and the ground-engaging surface. The ground-engaging surface may be formed by the cushioning layer. The ground-engaging surface may also be formed by an outsole layer that is attached to the cushioning layer.

With reference to the figures, an attachment system 10 for use with a prosthetic device 12 is provided. The prosthetic device 10 may be a foot prosthetic device and, further, may be a so-called prosthetic "blade" that may be attached to a lower portion of a person's leg. For example, the prosthetic blade 12 may be attached to a distal end of a prosthetic leg and is positioned to provide the person with support during walking and running movements. While the prosthetic device 12 could be any prosthetic device, the prosthetic device 12 will be described hereinafter as being a prosthetic blade.

The prosthetic blade 12 includes a proximal end 14 and a distal end 16 disposed on an opposite end of the prosthetic blade 12 than the proximal end 14. A body portion 18 extends between and connects the proximal end 14 and the distal end 16. The body portion 18 includes a generally curved shape and includes a substantially concave surface 20 and a substantially convex surface 22 disposed on an opposite side of the body portion 18 than the concave surface 20. The body portion 18 may be formed from metal and/or carbon fiber. The material of the body portion 18 along with its generally curved shape allow the prosthetic blade 12 to function as a spring during use which, in turn, provides a user with shock absorption and energy return during walking and running movements.

The proximal end 14 may include an attachment feature 24 for use in attaching the prosthetic blade 12 to a person's leg. For example, the attachment feature 24 may be an aperture that receives a fastener (not shown) for use in attaching the prosthetic blade 12 to a distal end of a prosthetic leg.

The attachment system includes a first component 26 and a second component 28 that cooperate to selectively attach a sole structure 30 to the prosthetic blade 12. The first component 26 is shown as being attached to the prosthetic blade 12 while the second component 28 is shown as being attached to the sole structure 30. While the first component 26 is shown as being attached to the prosthetic blade 12 and the second component 28 is shown as being attached to the sole structure 30, the first component 26 could alternatively be attached to the sole structure 30 and the second component 28 could be attached to the prosthetic blade 12.

The first component 26 includes a rail 32 that projects from the convex surface 22 of the body portion 18. The rail 32 may be integrally formed with the body portion 18 of the prosthetic blade 12 or, alternatively, may be fixedly attached to the body portion 18 at the convex surface 22. If the rail 32 is integrally formed with the body portion 18, the rail may be machined into the shape shown in FIGS. 2 and 3B. If the rail 32 is separately formed from the body potion 18, the rail 32 may be attached to the body portion 18 via a mechanical fastener such as a bolt and/or adhesive.

Figure 3A:
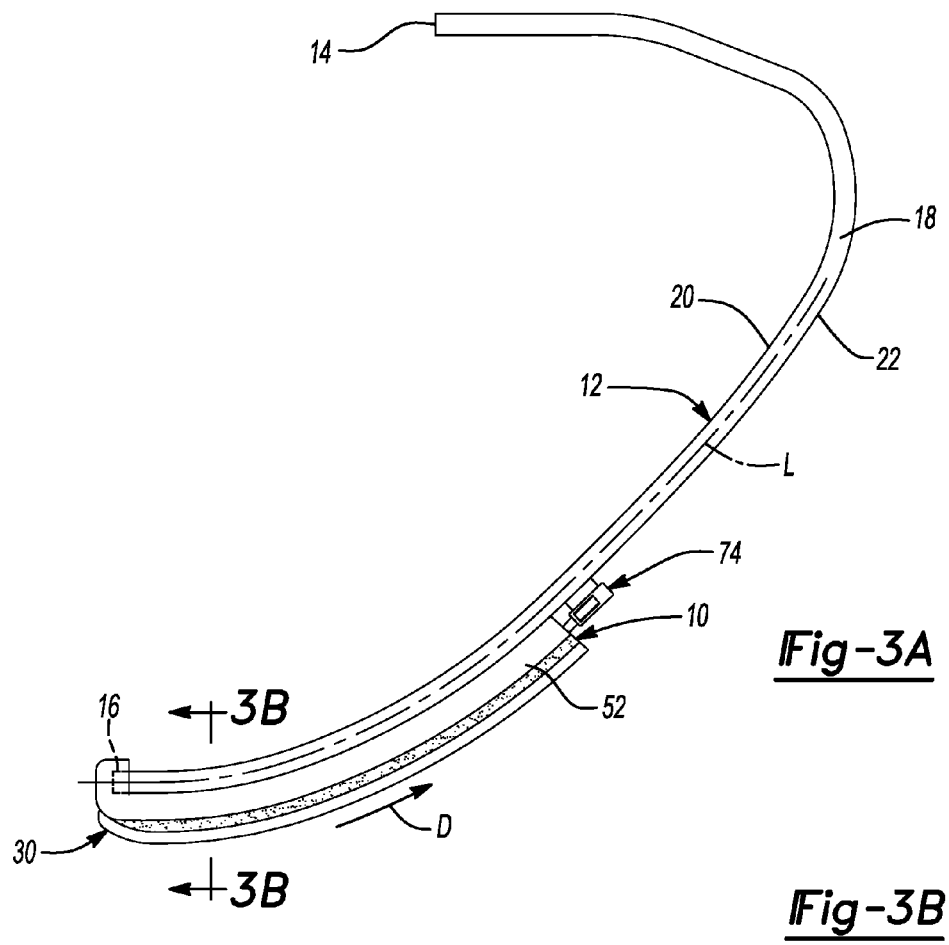
FIG. 3A is a side view of the prosthetic device of FIG. 1.
Figure 3B:
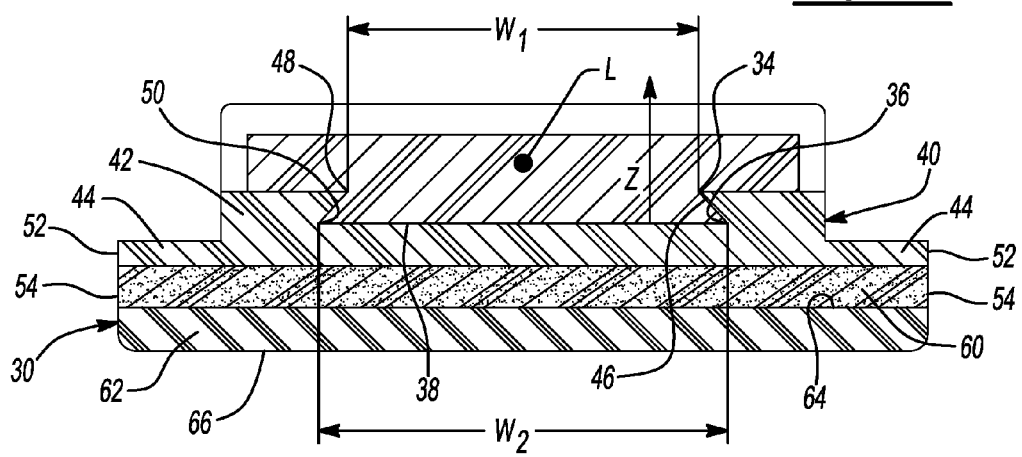
FIG. 3B is a cross-sectional view of the prosthetic device of FIG. 1 taken along line 3B-3B of FIG. 3A.

The rail 32 includes a projection extending from a first end 34 to a second end 36. The first end 34 is disposed adjacent to the convex surface 22 of the body portion 18 and includes a first width ($W_1$). The second end 36 is disposed at an opposite end of the rail 32 than the first end 34 and includes a second width ($W_2$). As shown in FIG. 3B, the second width ($W_2$) is larger than the first width ($W_1$).

In one configuration, the rail 32 is a tapered projection that has a constant taper extending from the first end 34 to the second end 36. Further, the rail 32 includes a substantially planar surface 38 disposed at the second end 36 and defining a width of the rail 32 at the second end. A length of the rail 32 extends from the distal end 16 of the body portion 18 in a direction toward the proximal end 14 of the body portion 18. The length is greater than the width and, as such, the rail 32 is an elongate component extending along a longitudinal axis (L) of the body portion 18.

The second component 28 includes a main body 40 having a projection 42 and a flange 44 extending from the projection 42. The main body 40 is disposed between and connects the first component 26 and the sole structure 30. Because the first component 26 is attached to the prosthetic blade 12, connecting the first component 26 to the sole structure 30 via the main body 40 likewise connects the sole structure 30 to the prosthetic blade 12.

The projection 42 extends in a direction away from the sole structure 30 toward the first component 26 and includes a channel 46 formed therein. The channel 46 extends along a length of the second component 28 and in a direction along the longitudinal axis (L) of the body portion 18 to a similar extent as the first component 26. As such, the second component 28 is similarly an elongate component. The channel 46 includes a shape that matingly receives the profile of the rail 32. Specifically, the channel 46 includes a first end 48 having a first width ($W_1$) and a second end 50 having a second with ($W_2$), whereby the first width ($W_1$) is less than the second width ($W_2$). If the first component 26 includes a tapered projection, the channel 46 may likewise include a taper that matches the taper of the first component 26 to allow the channel 46 to matingly receive the rail 32 of the first component 32. While the first component 26 and the second component 28 are both described as being elongate components, the first component 26 and the second component 28 may have the same length or different lengths. For example, the first component 26 may include a shorter or longer length than the second component 28. Further yet, second components 28 having different lengths may be used with the same first component 26 at different times to allow the first component 26 to be a universal component.

As shown in FIG. 3B, the flange 44 extends outward from the projection 42 and over the sole structure 30. The flange 44 defines an outer edge 52 that corresponds generally to an outer edge 54 of the sole structure 30. As such, the outer edge 52 of the flange 44 is substantially flush with the outer edge 54 of the sole structure 30. While the outer edge 52 is described and shown as being substantially flush with the outer edge 54, the outer edge 52 could alternatively be recessed from or extend over the outer edge 54.

Figure 2:
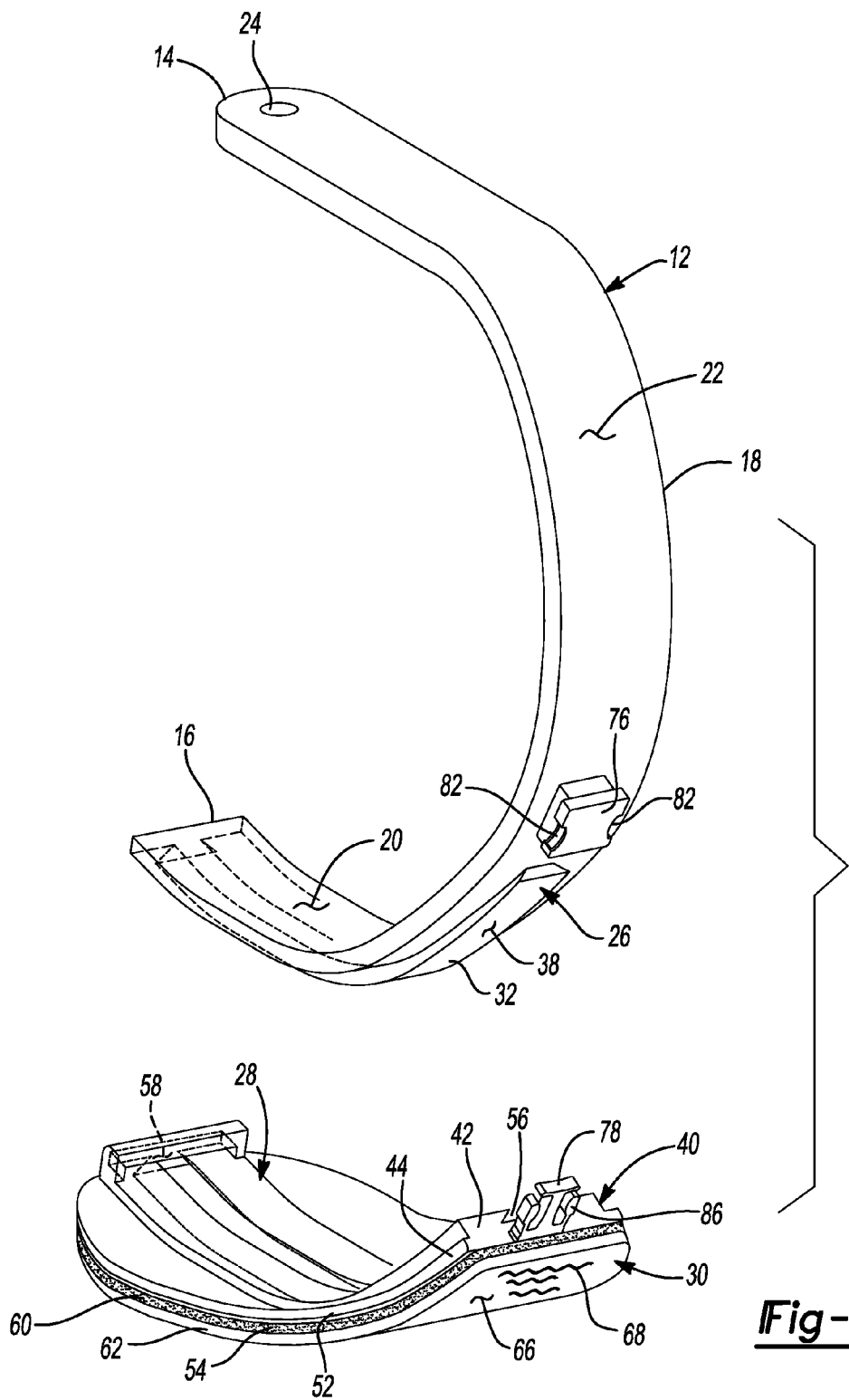
FIG. 2 is an exploded perspective view of the prosthetic device of FIG. 1 showing a first component of an attachment system separated from a second component of the attachment system.

In operation, the channel 46 slidably receives the rail 32 to attach the first component 26 to the second component 28 and, thus, the sole structure 30 to the prosthetic blade 12. Namely, the distal end 16 of the prosthetic blade 12 is first inserted into the channel 46 at an opening 56 of the channel 46 (FIG. 2). The second component 28 and, thus, the sole structure 30, are moved along and relative to the rail 32 until the distal end 16 of the prosthetic blade 12 contacts a stop surface 58 of the second component 28. Contact between the distal end 16 and the stop surface 58 prevents further movement of the second component 28 and sole structure 30 in a direction (D) shown in FIG. 3A. In this state, the sole structure 30 is attached and properly positioned relative to the prosthetic blade 12 via the attachment system 10.

The sole structure 30 is restricted from disengaging the prosthetic blade 12 due to the shape of the rail 32 and mating channel 46. Namely, because the width ($W_2$) is greater than the width ($W_1$), movement of the rail 32 and, thus, the prosthetic blade 12, in a direction (Z; FIG. 3B) relative to and away from the sole structure 30 is restricted. Specifically, if a force is exerted on the first component 26 in the direction (Z), the force is transmitted to the main body 40 of the second component 28 via the rail 32. The second component 28 moves with the rail 32 in the direction (Z) due to the shape of the rail 32 and channel 46. In one configuration, the rail 32 and the channel 46 cooperate to form a dovetail joint, thereby connecting the rail 32 and channel 46 together. This connection fixes the first component 26 to the second component 28 such that these components 26, 28 are fixed for movement in the Z direction.

While the shape of the rail 32 and the mating channel 46 are described and shown as including a dovetail joint, the rail 32 and mating channel 46 could have another shape. Namely, the rail 32 could have virtually any shape that includes a narrower cross section proximate to the prosthetic blade 12 than at the second end 36. For example, the rail 32 may include a stem and bulb configuration, whereby the stem is attached to the prosthetic blade 12 at the first end 34 and the bulb extends from the stem and defines the second end 36. Similarly, the rail 32 may include a cross section having a "T" shape with the stem of the "T" shape being connected to the prosthetic blade 12 and defining the first end 34 and the cross member of the "T" shape extending from the stem and defining the second end 36. Finally, the rail could include a circular or oval cross section with an outer perimeter attached to the prosthetic blade 12. Each of the foregoing configurations may be matingly received by a corresponding channel 46 to provide for slidable engagement between the first component 26 and the second component 28 while restricting disengagement between these components 26, 28 in the direction (Z).

Removal of the rail 32 from the channel 46 may be accomplished by applying a force on the second component in a direction opposite to direction (D). The force causes the rail 32 to slide relative to and within the channel 46 as the second component 28 moves in the direction opposite to direction (D). In so doing, the distal end 16 of the prosthetic blade 12 disengages and moves away from the stop surface 58. Movement of the second component 28 relative to the first component 26 continues until the rail 32 exits the channel 46 at the opening 56. At this point, the second component 28 and sole structure 30 are disconnected from the first component 26 and prosthetic blade 12.

The attachment system 10 may be used to attach different sole structures 30 to the prosthetic blade 12. For example, the attachment system 10 may be used to attach a particular sole structure 30 for use in a particular activity, thereby providing the user with a sole structure that is designed for the particular activity.

The sole structure 30 shown in FIG. 2 includes a midsole 60 and an outsole 62. The midsole 60 is disposed between the second component 28 and the outsole 62 and may be attached to both the second component 28 and the outsole via a suitable adhesive. Specifically, an adhesive may be applied to the flange 44 of the second component 28 on an opposite side of the second component 28 than the projection 42. Similarly, an adhesive may be applied to the outsole 62 at a surface 64 disposed on an opposite side of the outsole 62 than a ground-contacting surface 66. The adhesive attaches the midsole 60 to the second component 28 at the flange 44 and attaches the midsole 60 to the outsole 62 at the surface 64.

The midsole 60 provides a degree of cushioning to the sole structure 30 and may be formed from a foamed polymer material and/or may be a fluid-filled chamber. If the midsole 60 is a fluid-filled chamber, the midsole 60 may be formed by joining two sheets of polymer material together to define a chamber therebetween. The chamber may be filled with a fluid such as, for example, air, and may be pressurized. Regardless of the particular construction of the midsole 60, the midsole 60 is disposed between and is attached to the flange 44 on one side of the midsole 60 and is attached to the outsole 62 on the other side of the midsole 60. The materials and constructions of the midsole 60 are not limited to the described exemplary configurations. As such, other materials and constructions of midsole cushioning structures are also intended to be within the scope of the present disclosure.

The outsole 62 shown in FIG. 2 includes a series of treads 68. The treads 68 are formed into the material of the outsole 62 and provide the outsole 62 with a tread pattern suitable for walking and/or running on a substantially smooth surface (i.e., concrete or asphalt). The outsole 62 may be formed from an abrasion-resistant material such as, for example, rubber that provides a degree of friction between the outsole 62 and a ground surface or other underlying substrate surface during use. Alternatively, the outsole 62 can provide a degree of relatively low frictional engagement between the outsole and an underlying surface, such as an ice skating blade, a curling shoe outsole, a bowling shoe outsole, or other materials or constructions that allow sliding of a user's foot relative to an underlying surface as may be typical and beneficial during many activities, as will be recognized by a person of ordinary skill in the art in view of this description and the accompanying drawing figures. Further, the outsole 62 may include a binding or a cleat that is matingly received in a catch (none shown), to allow the outsole 62 and, thus, the sole structure 30 and prosthetic blade 12, to be attached to an external structure such as a bike pedal or ski boot binding.

The midsole 60 and the outsole 62 may also be used as a "spacer" that allows the prosthetic blade 12 to provide the user with an effective leg length that is approximately the same as the user's other leg. For example, a number of different second components 28 may be provided that each include a different thickness, as measured in a direction extending from the outsole 62 to the midsole 60. The different thicknesses of the various second components 28 allow the user to select a particular second component 28 that results in the effective length of the leg having the prosthetic blade 12 and sole structure 30 being the same as the user's other leg. Accordingly, the user can select the appropriate second component 28 based on the article of footwear in use on the user's other leg. For example, a second component 28 having a larger thickness could be used when the user's is wearing a high-heel shoe on the foot of the other leg to accommodate for the height of the high-heel shoe and a second component 28 having a reduced thickness could be used when the user is wearing a flat-bottom shoe on the foot of the other leg.

Figure 4A:
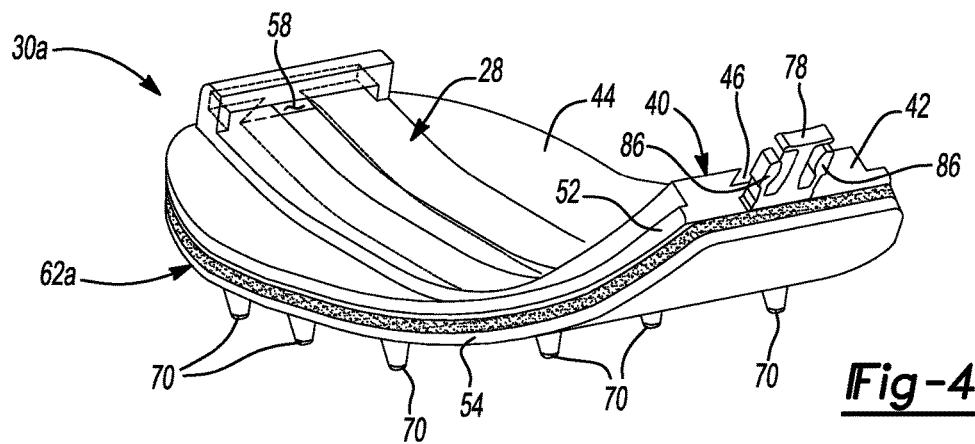
FIG. 4A is a perspective view of a sole structure for use with the prosthetic device of FIG. 1.

With particular reference to FIG. 4A, a sole structure 30a is provided and includes an outsole 62a having a series of cleats 70. In view of the substantial similarity in structure and function of the components associated with the sole structure 30 with respect to the sole structure 30a, like reference numerals are used hereinafter and in the drawings to identify like components while like reference numerals containing letter extensions are used to identify those components that have been modified.

The cleats 70 extend from the outsole 62a and provide the sole structure 30a with the ability to grip a ground surface such a natural or synthetic turf surface during use. As such, the sole structure 30a may be attached to the prosthetic blade 12 via the attachment system 10 when a user participates in an athletic activity such as football, soccer, or lacrosse.

Figure 4B:
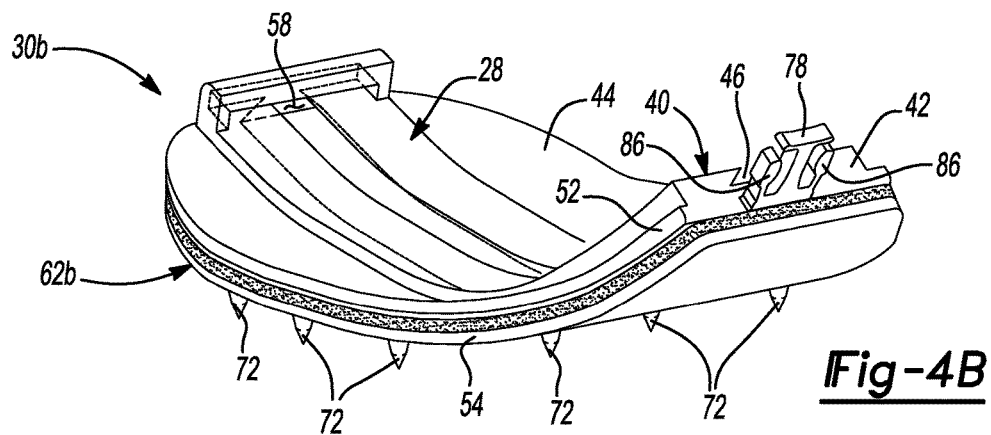
FIG. 4B is a perspective view of a sole structure for use with the prosthetic device of FIG. 1.

With particular reference to FIG. 4B, a sole structure 30b is provided and includes an outsole 62b having a series of spikes 72. In view of the substantial similarity in structure and function of the components associated with the sole structure 30b with respect to the sole structure 30, like reference numerals are used hereinafter and in the drawings to identify like components while like reference numerals containing letter extensions are used to identify those components that have been modified.

The spikes 72 extend from the outsole 62b and provide the sole structure 30b with the ability to grip a ground surface such a natural or synthetic track surface during use. As such, the sole structure 30b may be attached to the prosthetic blade 12 via the attachment system 10 when a user participates in an athletic activity such as a track-and-field competition.

Figure 4C:
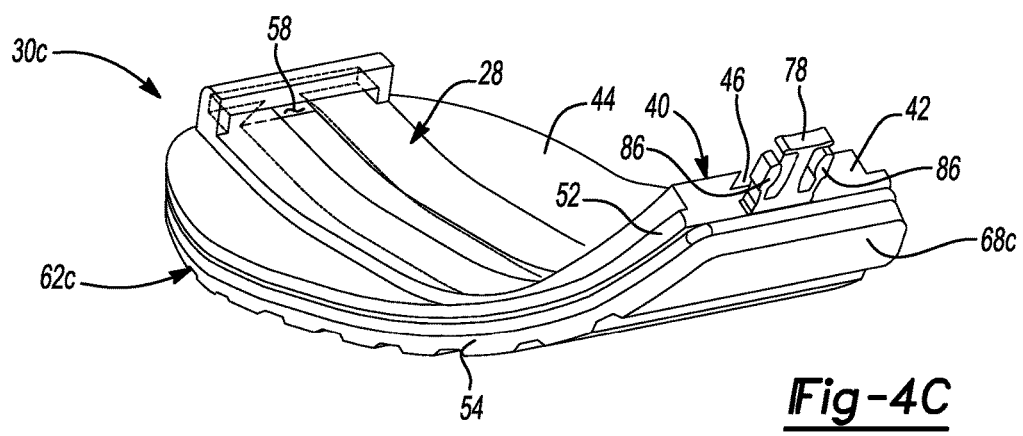
FIG. 4C is a perspective view of a sole structure for use with the prosthetic device of FIG. 1.

With particular reference to FIG. 4C, a sole structure 30c is provided and includes an outsole 62c having a series of treads 68c. In view of the substantial similarity in structure and function of the components associated with the sole structure 30c with respect to the sole structure 30, like reference numerals are used hereinafter and in the drawings to identify like components while like reference numerals containing letter extensions are used to identify those components that have been modified.

The treads 68c extend from the outsole 62 and provide the sole structure 30c with the ability to grip a ground surface such as loose dirt, rocks, and/or snow during use. As such, the sole structure 30c may be attached to the prosthetic blade 12 via the attachment system 10 when a user participates in an activity such as hiking.

The various sole structures 30, 30a, 30b, 30c may be selectively attached to the prosthetic blade 12 via the attachment system 10. Namely, each of the sole structures 30, 30a, 30b, 30c may include a dedicated second component 28 that allow the respective sole structures 30, 30a, 30b, 30c to be attached to the same rail 32 at different times. As such, the prosthetic blade 12 can include a single rail 32 but may be used with a variety of sole structures 30, 30a, 30b, 30c. Further, such sole structures 30, 30a, 30b, 30c are easily interchanged with one another by removing the rails 32 from one of the sole structures 30, 30a, 30b, 30c and attaching it to another of the sole structures 30, 30a, 30b, 30c. Providing the foregoing relationship between the rail 32 and the second component 28 of the various sole structures 30, 30a, 30b, 30c allows a user to quickly and easily change the sole structure 30, 30a, 30b, 30c attached to the prosthetic blade 12. As such, a user can quickly and easily tailor the prosthetic blade 12 for use in different activities (i.e., running, hiking, etc.).

As described above, the attachment system 10 utilizes a stop surface 58 of the second component 28 to properly position the second component 28 and the sole structure 30 relative to the first component 26 and prosthetic blade 12. The stop surface 58 ensures that the second component 28 and, thus, the sole structure 30 is moved a predetermined distance along the rail 32 to properly position the sole structure 30 relative to the prosthetic blade 12. The connection between the rail 32 and the channel 46 restricts detachment of the first component 26 from the second component 28 in the direction (Z; FIG. 3B). However, while the first component 26 and the second component 28 are attached to one another via interaction between the rail 32 and channel 46, movement of the second component along the rail 32

(i.e., along the longitudinal axis (L) of the prosthetic blade 12) is only restricted by the friction between the rail 32 and the channel 46.

A latch mechanism 74 may be used to fix a position of the second component 28 relative to the first component 26. Fixing a position of the second component 28 relative to the first component likewise fixes a position of the sole structure 30 relative to the prosthetic blade 12.

With reference to FIGS. 1, 2, and 5A-5C, the latch mechanism 74 includes a first latch component 76 attached to the prosthetic blade 12 and a second latch component 78 attached to the second component 28. While the first latch component 76 is shown and described as being attached to the prosthetic blade 12 and the second latch component 78 is shown and described as being attached to the second component 28, the first latch component 76 could alternatively be attached to the second component 28 and the second latch component 78 could alternatively be attached to the prosthetic blade 12.

The first latch component 76 includes an opening 80 and a pair of apertures 82 disposed on side surfaces of the latch component 76 and positioned substantially ninety degrees (90°) relative to the opening 80. The second latch mechanism 78 includes a locating tab 84 and a pair of latch elements 86 extending from a base 88. The second latch mechanism 78 may be formed from a resilient material such as, for example, plastic and may be movable from a relaxed state to a compressed state.

The first latch component 76 may be positioned relative to the rail 32 such that when the second component 28 is moved the predetermined distance relative to the first component 26 and the distal end 16 of the prosthetic blade 12 engages the stop surface 58, the second latch component 78 is received by the first latch component 76. Specifically, the locating tab 84 may enter the first latch component 74 and may guide the second latch component 78 into the first latch component 74.

Figure 5C:
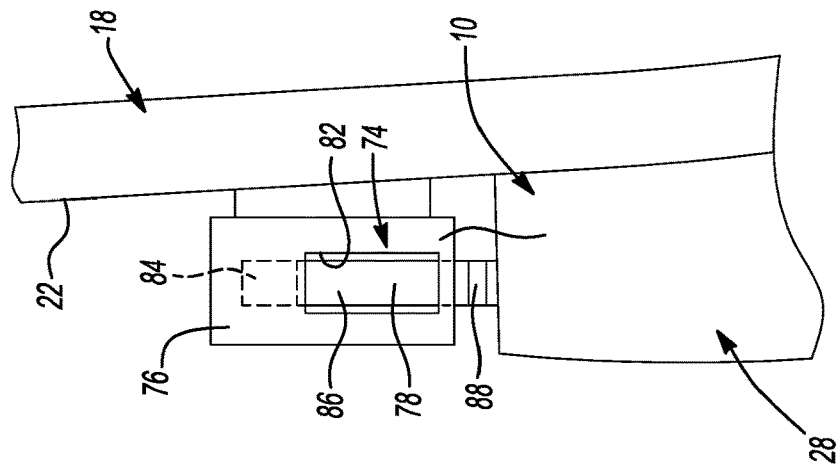
FIG. 5C is a side view of the latch mechanism of FIG. 5A shown in a latched state.
Figure 5B:
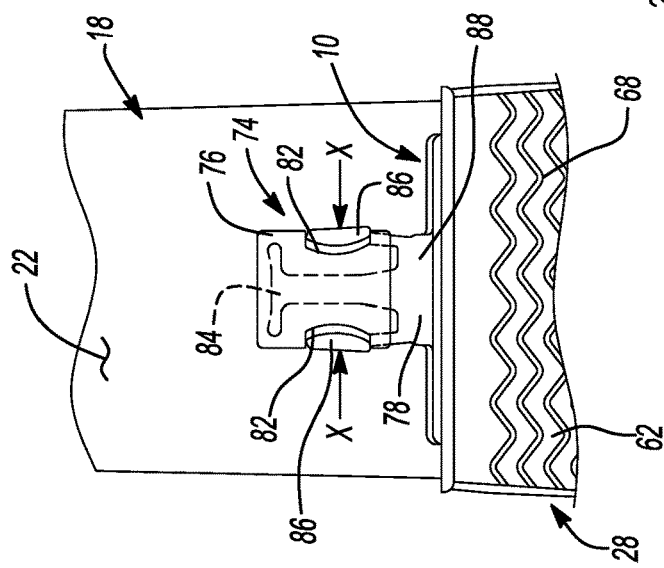
FIG. 5B is a top view of the latch mechanism of FIG. 5A shown in a latched state.
Figure 5A:
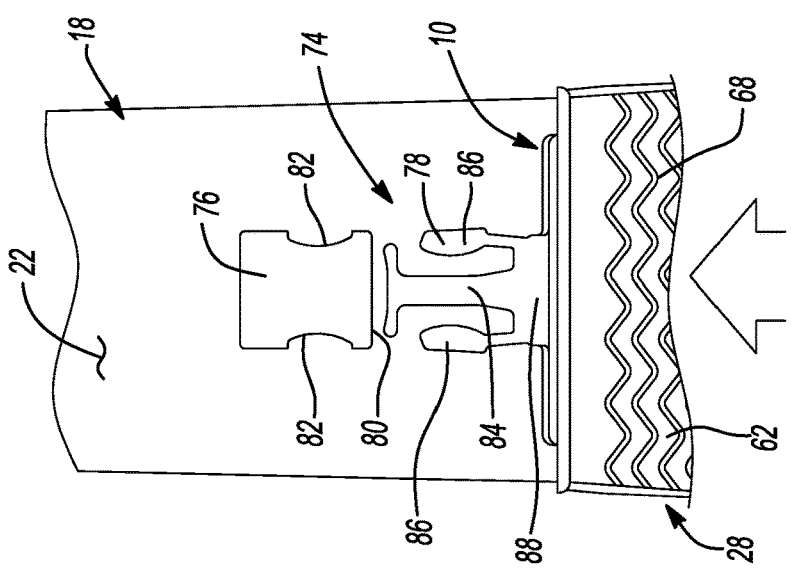
FIG. 5A is a top view of a latch mechanism for use with the prosthetic device of FIG. 1 shown in an unlatched state.

Once the second latch component 78 is sufficiently received by the first latch component 76, a force is applied to the latch elements 86 by walls 90 (FIG. 5C) of the first latch component 76 to move the latch elements 86 from the relaxed state to the compressed state. When the distal end 16 of the prosthetic blade 12 contacts the stop surface 58, the latch elements 86 oppose respective ones of the apertures 82. At this point, the resilient nature of the material of the second latch component 78 causes the latch elements 86 to automatically return to the relaxed state and protrude from the apertures 82 (FIG. 5B). At this point, the first component 76 and the second component 78 are attached to one another and relative movement therebetween is restricted due to engagement between the latch elements 86 and the respective apertures 82. Accordingly, relative movement between the first component 26 and the second component 28 along the longitudinal axis (L) of the prosthetic blade 12 is restricted and the position of the sole structure 30 relative to the prosthetic blade 12 is maintained.

The second latch component 78 may be removed from the first latch component 76 by applying a force on the latch elements 86 in a direction (X; FIG. 5B). Applying a force on the latch elements 86 in the direction (X) moves the latch elements 86 from the relaxed state to the compressed state and removes the latch elements 86 from the apertures 82. Once the latch elements 86 are removed from the apertures 82, the second latch component 78 may be removed from the first latch component 76 by moving the second latch component 78—along with the second component 28 and sole structure 30—in a direction away from the first latch component 76. Removing the second latch component 78 from the first latch component 76 allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30a, 30b, 30c.

With reference to FIGS. 6A-6C, another latch mechanism 74a for use with the attachment system 10 is provided. In view of the substantial similarity in structure and function of the components associated with the latch mechanism 74 with respect to the latch mechanism 74a, like reference numerals are used hereinafter and in the drawings to identify like components while like reference numerals containing letter extensions are used to identify those components that have been modified.

The latch mechanism 74a includes a first latch component 76a attached to the prosthetic blade 12 and a second latch component 78a attached to the second component 28. While the first latch component 76a is shown and described as being attached to the prosthetic blade 12 and the second latch component 78a is shown and described as being attached to the second component 28, the first latch component 76a could alternatively be attached to the second component 28 and the second latch component 78a could alternatively be attached to the prosthetic blade 12.

The first latch component 76a includes a notch 92 having an engagement surface 94. The second latch mechanism 78a includes a latch element 86a extending from a base 88a. The second latch mechanism 78a may be formed from a resilient material such as, for example, plastic and may be movable from a relaxed state to a flexed state.

The first latch component 76a may be positioned relative to the rail 32 such that when the second component 28 is moved the predetermined distance relative to the first component 26 and the distal end 16 of the prosthetic blade 12 engages the stop surface 58, the second latch component 78a is received by the first latch component 76a. Specifically, the latch element 86a is received by the notch 92 to fix a position of the second latch component 78a relative to the first latch component 76a.

Once the second latch component 78a is sufficiently received by the first latch component 76a, the latch element 86a is moved from the flexed state to the relaxed state and drops into the notch 92. Namely, a sloped surface 96 of the latch element 86a rides along the first latch component 76a and positions the latch element 86a in the flexed state. When the latch element 86a encounters the notch 92, the latch element 86a is automatically moved into the relaxed state due to the resilient nature of the material of the latch element 86a and drops into the notch 92. In so doing, a latch surface 98 of the latch element 86a engages the engagement surface 94 of the first latch component 76a, thereby fixing a position of the first component 26 relative to the second component 28. At this point, the first component 76a and the second component 78a are attached to one another and relative movement therebetween is restricted due to engagement between the latch element 86a and the engagement surface 94. Accordingly, relative movement between the first component 26 and the second component 28 along the longitudinal axis (L) of the prosthetic blade 12 is restricted and the position of the sole structure 30 relative to the prosthetic blade 12 is maintained.

The second latch component 78a may be removed from the first latch component 76a by applying a force on the latch element 86a in a direction (Y; FIG. 6C). Applying a force on the latch element 86a in the direction (Y) moves the latch element 86a from the relaxed state to the flexed state and removes the latch element 86a from the notch 92. Once the latch element 86a is removed from the notch 92, the second latch component 78a may be removed from the first latch component 76a by moving the second latch component 78a—along with the second component 28 and sole structure 30—in a direction away from the first latch component 76a. Removing the second latch component 78a from the first latch component 76a allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30a, 30b, 30c.

With reference to FIGS. 7A-7C, another latch mechanism 74b for use with the attachment system 10 is provided. In view of the substantial similarity in structure and function of the components associated with the latch mechanism 74 with respect to the latch mechanism 74b, like reference numerals are used hereinafter and in the drawings to identify like components while like reference numerals containing letter extensions are used to identify those components that have been modified.

The latch mechanism 74b includes a first latch component 76b attached to the prosthetic blade 12 and a second latch component 78b attached to the second component 28. While the first latch component 76b is shown and described as being attached to the prosthetic blade 12 and the second latch component 78b is shown and described as being attached to the second component 28, the first latch component 76b could alternatively be attached to the second component 28 and the second latch component 78b could alternatively be attached to the prosthetic blade 12.

The first latch component 76b includes a notch 92 having an engagement surface 94. The second latch mechanism 78b includes a latch element 86b extending from a base 88b. The second latch mechanism 78b may be formed from a resilient material such as, for example, plastic and may be movable from a relaxed state to a flexed state.

The first latch component 76b may be positioned relative to the rail 32 such that when the second component 28 is moved the predetermined distance relative to the first component 26 and the distal end 16 of the prosthetic blade 12 engages the stop surface 58, the second latch component 78b is received by the first latch component 76b. Specifically, the latch element 86b is received by the notch 92 to fix a position of the second latch component 78b relative to the first latch component 76b. Alignment of the latch element 86b and the notch 92 may be further achieved by engaging projections 100 of the second latch component 78b with stops 102 of the first latch component 76b.

Once the second latch component 78b is sufficiently received by the first latch component 76b, the latch element 86b is moved from the flexed state to the relaxed state and drops into the notch 92. Namely, a sloped surface 96 of the latch element 86b rides along the first latch component 76b and positions the latch element 86b in the flexed state. When the latch element 86b encounters the notch 92, the latch element 86b is automatically moved into the relaxed state due to the resilient nature of the material of the latch element 86b and drops into the notch 92. In so doing, a latch surface 98 of the latch element 86b engages the engagement surface 94 of the first latch component 76b, thereby fixing a position of the first component 26 relative to the second component 28. At this point, the first component 76b and the second component 78b are attached to one another and relative movement therebetween is restricted due to engagement between the latch element 86b and the engagement surface 94. Accordingly, relative movement between the first component 26 and the second component 28 along the longitudinal axis (L) of the prosthetic blade 12 is restricted and the position of the sole structure 30 relative to the prosthetic blade 12 is maintained.

The second latch component 78b may be removed from the first latch component 76b by applying a force on the latch element 86b in a direction (W; FIG. 7D). Applying a force on the latch element 86b in the direction (W) moves the latch element 86b from the relaxed state to the flexed state and removes the latch element 86b from the notch 92. Once the latch element 86b is removed from the notch 92, the second latch component 78b may be removed from the first latch component 76b by moving the second latch component 78b—along with the second component 28 and sole structure 30—in a direction away from the first latch component 76b. Removing the second latch component 78b from the first latch component 76b allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30a, 30b, 30c.

With reference to FIGS. 8A-8C, another latch mechanism 74c for use with the attachment system 10 is provided. In view of the substantial similarity in structure and function of the components associated with the latch mechanism 74 with respect to the latch mechanism 74c, like reference numerals are used hereinafter and in the drawings to identify like components while like reference numerals containing letter extensions are used to identify those components that have been modified.

The latch mechanism 74c includes a first latch component 76c attached to the prosthetic blade 12 and a second latch component 78c attached to the second component 28. While the first latch component 76c is shown and described as being attached to the prosthetic blade 12 and the second latch component 78c is shown and described as being attached to the second component 28, the first latch component 76c could alternatively be attached to the second component 28 and the second latch component 78c could alternatively be attached to the prosthetic blade 12.

The first latch component 76c includes a channel 104 having an engagement surface 94c and a ramped surface 106. The second latch mechanism 78c includes a latch element 86c extending from a base 88c. The second latch mechanism 78c may be formed from a resilient material such as, for example, plastic and may be movable from a relaxed state to a flexed state.

The first latch component 76c may be positioned relative to the rail 32 such that when the second component 28 is moved the predetermined distance relative to the first component 26 and the distal end 16 of the prosthetic blade 12 engages the stop surface 58, the second latch component 78c is received by the first latch component 76c. Specifically, the latch element 86c is received by the channel 104 to fix a position of the second latch component 78c relative to the first latch component 76c.

Once the second latch component 78c is sufficiently received by the first latch component 76c, the latch element 86c is moved from the relaxed state to the flexed state when the sloped surface 96 engages the ramped surface 106. The latch element 86c remains in the flexed state until the latch element 86c traverses the channel 104 and the latch surface 98 engages the engagement surface 94c. Namely, the sloped surface 96 of the latch element 86c rides along the ramped surface 106 and positions the latch element 86c in the flexed state. When the latch element 86c traverses the entire channel 104, the latch element 86c is automatically moved into the relaxed state due to the resilient nature of the material of the latch element 86c and is positioned in the configuration shown in FIG. 8C. In so doing, the latch surface 98 of the latch element 86c engages the engagement surface 94c of the first latch component 76c, thereby fixing a position of the first component 26 relative to the second component 28. At this point, the first component 76c and the second component 78c are attached to one another and relative movement therebetween is restricted due to engagement between the latch element 86c and the engagement surface 94c. Accordingly, relative movement between the first component 26 and the second component 28 along the longitudinal axis (L) of the prosthetic blade 12 is restricted and the position of the sole structure 30 relative to the prosthetic blade 12 is maintained.

The second latch component 78c may be removed from the first latch component 76c by applying a force on the latch element 86c in a direction (Q; FIG. 8C). Applying a force on the latch element 86c in the direction (Q) moves the latch element 86c from the relaxed state to the flexed state and removes the latch element 86c from engagement with the engagement surface 94c. Once the latch element 86c is removed from engagement with the engagement surface 94c, the second latch component 78c may be removed from the first latch component 76c by moving the second latch component 78c—along with the second component 28 and sole structure 30—in a direction away from the first latch component 76c. Removing the second latch component 78c from the first latch component 76c allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30a, 30b, 30c.

With reference to FIGS. 9A-9C, another latch mechanism 74d for use with the attachment system 10 is provided. In view of the substantial similarity in structure and function of the components associated with the latch mechanism 74 with respect to the latch mechanism 74d, like reference numerals are used hereinafter and in the drawings to identify like components while like reference numerals containing letter extensions are used to identify those components that have been modified.

The latch mechanism 74d includes a first latch component 76d attached to the prosthetic blade 12 and a second latch component 78d attached to the second component 28. While the first latch component 76d is shown and described as being attached to the prosthetic blade 12 and the second latch component 78d is shown and described as being attached to the second component 28, the first latch component 76d could alternatively be attached to the second component 28 and the second latch component 78d could alternatively be attached to the prosthetic blade 12.

The second latch component 78d includes a latch element 86d extending from a base 88d. The second latch mechanism 78d may be formed from a resilient material such as, for example, plastic and/or rubber and may be movable from a relaxed state to a flexed state.

The first latch component 76d may be positioned relative to the rail 32 such that when the second component 28 is moved the predetermined distance relative to the first component 26 and the distal end 16 of the prosthetic blade 12 engages the stop surface 58, the second latch component 78d is positioned proximate to the first latch component 76d. Specifically, the latch element 86d opposes a projection 108 of the first latch component 76d and may be attached to the projection 108 to fix a position of the second latch component 78d relative to the first latch component 76d.

Once the second latch component 78d is sufficiently attached to the first latch component 76d, the latch element 86d is moved from the relaxed state to the flexed state. Specifically, a force may be applied to the latch element 86d to move the latch element 86d from the relaxed state (FIG. 9C) to the flexed state (FIGS. 9A and 9B) and into engagement with the projection 108 of the first latch component 76d.

The latch element 86d may include a hook 110 that is received by a recess 112 of the first latch component 76d when the latch element 86d is returned to the relaxed state. At this point, the first component 76d and the second component 78d are attached to one another and relative movement therebetween is restricted due to engagement between the hook 110 of the latch element 86d and the recess 110 of the first latch component 76d. Accordingly, relative movement between the first component 26 and the second component 28 along the longitudinal axis (L) of the prosthetic blade 12 is restricted and the position of the sole structure 30 relative to the prosthetic blade 12 is maintained.

The second latch component 78d may be removed from the first latch component 76d by applying a force on the latch element 86d in a direction (R; FIG. 9C). Applying a force on the latch element 86d in the direction (R) moves the latch element 86d from the relaxed state to the flexed state and removes the latch element 86d from engagement with the recess 112. Once the latch element 86d is removed from engagement with the recess 112, the second latch component 78d may be removed from the first latch component 76d by moving the second latch component 78d—along with the second component 28 and sole structure 30—in a direction away from the first latch component 76d. Removing the second latch component 78d from the first latch component 76d allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30a, 30b, 30c.

With reference to FIGS. 10A-10C, another latch mechanism 74e for use with the attachment system 10 is provided. In view of the substantial similarity in structure and function of the components associated with the latch mechanism 74 with respect to the latch mechanism 74e, like reference numerals are used hereinafter and in the drawings to identify like components while like reference numerals containing letter extensions are used to identify those components that have been modified.

The latch mechanism 74e includes a first latch component 76e attached to the prosthetic blade 12 and a second latch component 78e attached to the second component 28. While the first latch component 76e is shown and described as being attached to the prosthetic blade 12 and the second latch component 78e is shown and described as being attached to the second component 28, the first latch component 76e could alternatively be attached to the second component 28 and the second latch component 78e could alternatively be attached to the prosthetic blade 12.

The first latch component 76e includes a notch 92e having an engagement surface 94e (FIG. 10B) and a magnet 114 located on an opposite side of the first latch component 76e than the notch 92e. As shown in FIGS. 10B and 10C, the notch 92e and magnet 114 may be located on opposite sides of the body portion 18 of the prosthetic blade 12 such that the notch 92e is formed into the material of the body portion 18 and the magnet 114 is recessed into the body portion 18. The second latch mechanism 78e includes a projection 116 extending from a base 88e and including at least a portion formed from metal. The base 88e and at least a portion of the projection 116 of the second latch mechanism 78e may be formed from a resilient material such as, for example, plastic and may be movable from a relaxed state to a flexed state.

The first latch component 76e may be positioned relative to the rail 32 such that when the second component 28 is moved the predetermined distance relative to the first component 26 and the distal end 16 of the prosthetic blade 12 engages the stop surface 58, the second latch component 78e is received by the first latch component 76e. Specifically, the latch element 86e is received by the notch 92e to fix a position of the second latch component 78e relative to the first latch component 76e.

Once the second latch component 78e is sufficiently received by the first latch component 76e, the latch element 86e is moved from the flexed state to the relaxed state and drops into the notch 92e. Namely, the projection 116 of the latch element 86e rides along the first latch component 76e and positions the latch element 86e in the flexed state. When the latch element 86e encounters the notch 92e, the latch element 86e is automatically moved into the relaxed state due to the resilient nature of the material of the latch element 86e and due to the magnet exerting a force on the projection 116 and drops into the notch 92e. In so doing, a latch surface 98e of the latch element 86e engages the engagement surface 94e of the first latch component 76e, thereby fixing a position of the first component 26 relative to the second component 28. At this point, the first component 76e and the second component 78e are attached to one another and relative movement therebetween is restricted due to engagement between the latch element 86e and the engagement surface 94e. Accordingly, relative movement between the first component 26 and the second component 28 along the longitudinal axis (L) of the prosthetic blade 12 is restricted and the position of the sole structure 30 relative to the prosthetic blade 12 is maintained.

The second latch component 78e may be removed from the first latch component 76e by applying a force on the latch element 86e in a direction (S; FIG. 10C). Applying a force on the latch element 86e in the direction (S) moves the latch element 86e from the relaxed state to the flexed state and removes the latch element 86e from the notch 92e. Once the latch element 86e is removed from the notch 92e, the second latch component 78e may be removed from the first latch component 76e by moving the second latch component 78e—along with the second component 28 and sole structure 30—in a direction away from the first latch component 76e. Removing the second latch component 78e from the first latch component 76e allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30a, 30b, 30c.

With reference to FIGS. 11A-11C, another latch mechanism 74f for use with the attachment system 10 is provided. In view of the substantial similarity in structure and function of the components associated with the latch mechanism 74 with respect to the latch mechanism 74f, like reference numerals are used hereinafter and in the drawings to identify like components while like reference numerals containing letter extensions are used to identify those components that have been modified.

The latch mechanism 74f includes a first latch component 76f attached to the prosthetic blade 12 and a second latch component 78f attached to the second component 28. While the first latch component 76f is shown and described as being attached to the prosthetic blade 12 and the second latch component 78f is shown and described as being attached to the second component 28, the first latch component 76f could alternatively be attached to the second component 28 and the second latch component 78f could alternatively be attached to the prosthetic blade 12.

The first latch component 76f includes a channel 104f and a projection 118 including an engagement surface 94f formed at a distal end thereof extending into the channel 104f. The second latch mechanism 78f includes a latch element 86f extending from a base 88f and including a series of peaks 120 and depressions 122 formed between adjacent peaks 120.

The first latch component 76f may be positioned relative to the rail 32 such that when the second component 28 is moved the predetermined distance relative to the first component 26 and the distal end 16 of the prosthetic blade 12 engages the stop surface 58, the second latch component 78f is received by the first latch component 76f. Specifically, the latch element 86f is received by the channel 104f to fix a position of the second latch component 78f relative to the first latch component 76f.

Once the second latch component 78f is sufficiently received by the first latch component 76f, the latch element 86f is moved into engagement with the engagement surface 94f of the projection 118. Namely, the projection 118 moves along the latch element 86f and is received within depressions 122 formed between adjacent peaks 120. The latch element 86f may be received within any of the depressions 122 depending on the extent to which the latch element 86f extends into the channel 104f. Once movement of the latch element 86f into the channel 104f is stopped and the projection 118 is received within a depression 122, the first component 76f and the second component 78f are attached to one another and relative movement therebetween is restricted due to engagement between the latch element 86f and the engagement surface 94f of the projection 118. Accordingly, relative movement between the first component 26 and the second component 28 along the longitudinal axis (L) of the prosthetic blade 12 is restricted and the position of the sole structure 30 relative to the prosthetic blade 12 is maintained.

The second latch component 78f may be removed from the first latch component 76f by applying a force on a release tab 124 to depress the release tab 124 and remove the projection 118 from engagement with the depressions 120. Specifically, the applied force causes the projection 118 to move in the direction (T) and away from the latch element 86f. Once the engagement surface 94f of the projection 118 is removed from engagement with the latch element 86f, the second latch component 78f may be removed from the first latch component 76f by moving the second latch component 78f—along with the second component 28 and sole structure 30—in a direction away from the first latch component 76f. Removing the second latch component 78f from the first latch component 76f allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30a, 30b, 30c.

With reference to FIGS. 12A-12B, another latch mechanism 74g for use with the attachment system 10 is provided.

In view of the substantial similarity in structure and function of the components associated with the latch mechanism 74 with respect to the latch mechanism 74g, like reference numerals are used hereinafter and in the drawings to identify like components while like reference numerals containing letter extensions are used to identify those components that have been modified.

The latch mechanism 74g includes a first latch component 76g attached to the prosthetic blade 12 and a second latch component 78g attached to the second component 28. While the first latch component 76g is shown and described as being attached to the prosthetic blade 12 and the second latch component 78g is shown and described as being attached to the second component 28, the first latch component 76g could alternatively be attached to the second component 28 and the second latch component 78g could alternatively be attached to the prosthetic blade 12.

The first latch component 76g includes a buckle 126. The first latch component 76g may be positioned relative to the rail 32 such that when the second component 28 is moved the predetermined distance relative to the first component 26 and the distal end 16 of the prosthetic blade 12 engages the stop surface 58, the second latch component 78g is positioned proximate to the first latch component 76g. Specifically, the buckle 126 receives a belt portion 128 of the second latch component 78g and may be attached to the belt portion 128 to fix a position of the second latch component 78g relative to the first latch component 76g.

The buckle 124 may include a post 130 that is received by one of a series of apertures 132 associated with the belt portion 128. When the post 130 is received in one of the apertures 132, the position of the belt portion 128 relative to the buckle 126 is substantially fixed. At this point, the first latch component 76g and the second latch component 78g are attached to one another and relative movement therebetween is restricted due to engagement between the buckle 126 and the belt portion 128. Accordingly, relative movement between the first component 26 and the second component 28 along the longitudinal axis (L) of the prosthetic blade 12 is restricted and the position of the sole structure 30 relative to the prosthetic blade 12 is maintained.

The second latch component 78g may be removed from the first latch component 76g by applying a force on the post 130 to remove the post 120 from the belt portion 128. Once the post 130 is removed from engagement with the belt portion 128, the second latch component 78g may be removed from the first latch component 76g by moving the second latch component 78g—along with the second component 28 and sole structure 30—in a direction away from the first latch component 76g. Removing the second latch component 78g from the first latch component 76g allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30a, 30b, 30c.

With reference to FIGS. 13A-13B, another latch mechanism 74h for use with the attachment system 10 is provided. In view of the substantial similarity in structure and function of the components associated with the latch mechanism 74 with respect to the latch mechanism 74g, like reference numerals are used hereinafter and in the drawings to identify like components while like reference numerals containing letter extensions are used to identify those components that have been modified.

The latch mechanism 74h includes a first latch component 76h attached to the prosthetic blade 12 and a second latch component 78h attached to the second component 28. While the first latch component 76h is shown and described as being attached to the prosthetic blade 12 and the second latch component 78h is shown and described as being attached to the second component 28, the first latch component 76h could alternatively be attached to the second component 28 and the second latch component 78h could alternatively be attached to the prosthetic blade 12.

The first latch component 76h includes a latch post 134. The first latch component 76h may be positioned relative to the rail 32 such that when the second component 28 is moved the predetermined distance relative to the first component 26 and the distal end 16 of the prosthetic blade 12 engages the stop surface 58, the second latch component 78h is positioned proximate to the first latch component 76h. Specifically, the latch post 134 may be inserted into one of a series of apertures 132 of the belt portion 128 to fix a position of the second latch component 78h relative to the first latch component 76h.

When the latch post 134 is received in one of the apertures 132, the position of the belt portion 128 relative to the first latch component 76h is substantially fixed. At this point, the first latch component 76h and the second latch component 78h are attached to one another and relative movement therebetween is restricted due to engagement between the latch post 134 and the belt portion 128. Accordingly, relative movement between the first component 26 and the second component 28 along the longitudinal axis (L) of the prosthetic blade 12 is restricted and the position of the sole structure 30 relative to the prosthetic blade 12 is maintained.

The second latch component 78h may be removed from the first latch component 76h by removing the latch post 134 from the belt portion 128. Once the post 134 is removed from engagement with the belt portion 128, the second latch component 78h may be removed from the first latch component 76h by moving the second latch component 78h—along with the second component 28 and sole structure 30—in a direction away from the first latch component 76h. Removing the second latch component 78h from the first latch component 76h allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30a, 30b, 30c.

With reference to FIGS. 14A-14C, another latch mechanism 74i for use with the attachment system 10 is provided. In view of the substantial similarity in structure and function of the components associated with the latch mechanism 74 with respect to the latch mechanism 74i, like reference numerals are used hereinafter and in the drawings to identify like components while like reference numerals containing letter extensions are used to identify those components that have been modified.

The latch mechanism 74i includes a first latch component 76i attached to the prosthetic blade 12 and a second latch component 78i attached to the second component 28. While the first latch component 76i is shown and described as being attached to the prosthetic blade 12 and the second latch component 78i is shown and described as being attached to the second component 28, the first latch component 76i could alternatively be attached to the second component 28 and the second latch component 78i could alternatively be attached to the prosthetic blade 12.

The first latch component 76i includes a channel 104i and a recess 136 in communication with the channel 104i. The second latch mechanism 78i includes a latch element 86i in selective engagement with a plunger 140. The plunger 140 is disposed within the recess 136 and extends into the channel 104i. The plunger 140 is biased in the direction (M) shown in FIG. 14B by a biasing member 142. The biasing member 142 may be a coil spring that acts on the plunger 142 to bias the plunger 140 into the channel 104i.

The first latch component 76i may be positioned relative to the rail 32 such that when the second component 28 is moved the predetermined distance relative to the first component 26 and the distal end 16 of the prosthetic blade 12 engages the stop surface 58, the second latch component 78i is received by the first latch component 76i. Specifically, the latch element 86i is received by the channel 104i to fix a position of the second latch component 78i relative to the first latch component 76i.

Once the second latch component 78i is sufficiently received by the first latch component 76i, the latch element 86i is moved into the channel 104i and into engagement with the plunger 140. Namely, the latch element 86i moves the plunger 140 in a direction opposite to direction (M) upon first entering the channel 104i. Once movement of the latch element 86i into the channel 104i is stopped due to the distal end 16 of the prosthetic blade 12 engaging the stop surface 58, the plunger 140 is received by one of a series of detents 138 formed in the latch element 86i. Once movement of the latch element 86i into the channel 104i is stopped and the plunger 140 is received within a detent 138, the first component 76i and the second component 78i are attached to one another and relative movement therebetween is restricted. Accordingly, relative movement between the first component 26 and the second component 28 along the longitudinal axis (L) of the prosthetic blade 12 is restricted and the position of the sole structure 30 relative to the prosthetic blade 12 is maintained.

The second latch component 78i may be removed from the first latch component 76i by applying a force on the plunger 140 in a direction opposite to direction (M) and against the force exerted on the plunger 140 by the biasing member 142. Once the plunger 140 is removed from the detent 138, the second latch component 78i may be removed from the first latch component 76i by moving the second latch component 78i—along with the second component 28 and sole structure 30—in a direction away from the first latch component 76i. Removing the second latch component 78i from the first latch component 76i allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30a, 30b, 30c.

With reference to FIGS. 15A-15C, another latch mechanism 74j for use with the attachment system 10 is provided. In view of the substantial similarity in structure and function of the components associated with the latch mechanism 74 with respect to the latch mechanism 74j, like reference numerals are used hereinafter and in the drawings to identify like components while like reference numerals containing letter extensions are used to identify those components that have been modified.

The latch mechanism 74j includes a first latch component 76j attached to the prosthetic blade 12 and a second latch component 78j attached to the second component 28. While the first latch component 76j is shown and described as being attached to the prosthetic blade 12 and the second latch component 78j is shown and described as being attached to the second component 28, the first latch component 76j could alternatively be attached to the second component 28 and the second latch component 78j could alternatively be attached to the prosthetic blade 12.

The first latch component 76j includes a recess 144 receiving a ball 146 and a biasing member 148 therein. The biasing member 148 biases the ball 146 in a direction (N) in a direction away from the recess 144. The second latch mechanism 78j includes a socket 150 extending into the second latch component 78j.

The first latch component 76j may be positioned relative to the rail 32 such that when the second component 28 is moved the predetermined distance relative to the first component 26 and the distal end 16 of the prosthetic blade 12 engages the stop surface 58, the ball 146 is automatically received by socket 150 due to the biasing force exerted on the ball 146 by the biasing member 148.

Once the ball 146 is sufficiently received by the socket 150, a position of the first component 26 relative to the second component 28 is fixed. At this point, the first component 76j and the second component 78j are attached to one another and relative movement therebetween is restricted. Accordingly, relative movement between the first component 26 and the second component 28 along the longitudinal axis (L) of the prosthetic blade 12 is restricted and the position of the sole structure 30 relative to the prosthetic blade 12 is maintained.

The second latch component 78j may disengaged from the ball 146 by moving the second latch component 78j—along with the second component 28 and sole structure 30—in a direction away from the first latch component 76j. Removing the socket 150 from the ball 146 allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30a, 30b, 30c.

With reference to FIGS. 16A-16C, another latch mechanism 74k for use with the attachment system 10 is provided. In view of the substantial similarity in structure and function of the components associated with the latch mechanism 74 with respect to the latch mechanism 74k, like reference numerals are used hereinafter and in the drawings to identify like components while like reference numerals containing letter extensions are used to identify those components that have been modified.

The latch mechanism 74k includes a first latch component 76k attached to the prosthetic blade 12 and a second latch component 78k attached to the second component 28. While the first latch component 76k is shown and described as being attached to the prosthetic blade 12 and the second latch component 78k is shown and described as being attached to the second component 28, the first latch component 76k could alternatively be attached to the second component 28 and the second latch component 78k could alternatively be attached to the prosthetic blade 12.

The first latch component 76k includes a channel 104k and a recess 136k in communication with the channel 104k. The second latch mechanism 78k includes a latch element 86k in selective engagement with a plunger 140k. The plunger 140k is disposed within the recess 136k and extends into the channel 104k. The plunger 140k is biased in the direction (0) shown in FIG. 16A by a biasing member 142k. The biasing member 142k may be a coil spring that acts on the plunger 142k to bias the plunger 140k into the channel 104k.

The first latch component 76k may be positioned relative to the rail 32 such that when the second component 28 is moved the predetermined distance relative to the first component 26 and the distal end 16 of the prosthetic blade 12 engages the stop surface 58, the second latch component 78k is received by the first latch component 76k. Specifically, the latch element 86k is received by the channel 104k to fix a position of the second latch component 78k relative to the first latch component 76k.

Once the second latch component 78k is sufficiently received by the first latch component 76k, the latch element 86k is moved into the channel 104k and into engagement with the plunger 140k. Namely, the latch element 86k moves the plunger 140k in a direction opposite to direction (O) upon first entering the channel 104k at a rounded, distal end 152 of the latch element 86k. Once movement of the latch element 86k into the channel 104k is stopped due to the distal end 16 of the prosthetic blade 12 engaging the stop surface 58, the plunger 140k is received by an aperture 154 formed in the latch element 86k. Once movement of the latch element 86k into the channel 104k is stopped and the plunger 140k is received within the aperture 154, the first component 76k and the second component 78k are attached to one another and relative movement therebetween is restricted. Accordingly, relative movement between the first component 26 and the second component 28 along the longitudinal axis (L) of the prosthetic blade 12 is restricted and the position of the sole structure 30 relative to the prosthetic blade 12 is maintained.

The second latch component 78k may be removed from the first latch component 76k by applying a force on the plunger 140k in a direction opposite to direction (O) and against the force exerted on the plunger 140k by the biasing member 142k. Once the plunger 140k is removed from the aperture 154, the second latch component 78k may be removed from the first latch component 76k by moving the second latch component 78k—along with the second component 28 and sole structure 30—in a direction away from the first latch component 76k. Removing the second latch component 78k from the first latch component 76k allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30a, 30b, 30c.

With reference to FIGS. 17A-17C, another latch mechanism 74l for use with the attachment system 10 is provided. In view of the substantial similarity in structure and function of the components associated with the latch mechanism 74 with respect to the latch mechanism 74l, like reference numerals are used hereinafter and in the drawings to identify like components while like reference numerals containing letter extensions are used to identify those components that have been modified.

The latch mechanism 74l includes a first latch component 76l attached to the prosthetic blade 12 and a second latch component 78l attached to the second component 28. While the first latch component 76l is shown and described as being attached to the prosthetic blade 12 and the second latch component 78l is shown and described as being attached to the second component 28, the first latch component 76l could alternatively be attached to the second component 28 and the second latch component 78l could alternatively be attached to the prosthetic blade 12.

The first latch component 76l includes a post 156 having a pair of projections 158 defining a pair of detents 160. The second latch component 76l includes a pair of extensions 162 formed from a flexible material and extending into a channel 164.

The first latch component 76l may be positioned relative to the rail 32 such that when the second component 28 is moved the predetermined distance relative to the first component 26 and the distal end 16 of the prosthetic blade 12 engages the stop surface 58, the second latch component 78l receives the first latch component 76l. Specifically, the post 156 is received by the channel 164 with the extensions 162 sliding along respective outer surfaces 168 of the post 156. Because the extensions 162 are formed from a flexible material, the extensions 162 bend into the shape shown in FIG. 17A. The extensions 162, upon encountering the projections 158 bend further until being received within respective detents 160. At this point, a position of the second latch component 78l relative to the first latch component 76l is fixed.

The second latch component 78l may be removed from the first latch component 76l by moving the second latch component 78l—along with the second component 28 and sole structure 30—in a direction away from the first latch component 76l to allow the extensions 162 to disengage the detents 160 and once again slide along the surfaces 168 of the post 156. Removing the second latch component 78l from the first latch component 76lk allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30a, 30b, 30c.

With reference to FIGS. 18A-18C, another latch mechanism 74m for use with the attachment system 10 is provided. In view of the substantial similarity in structure and function of the components associated with the latch mechanism 74 with respect to the latch mechanism 74m, like reference numerals are used hereinafter and in the drawings to identify like components while like reference numerals containing letter extensions are used to identify those components that have been modified.

The latch mechanism 74m includes a first latch component 76m attached to the prosthetic blade 12 and a second latch component 78m attached to the second component 28. While the first latch component 76m is shown and described as being attached to the prosthetic blade 12 and the second latch component 78m is shown and described as being attached to the second component 28, the first latch component 76m could alternatively be attached to the second component 28 and the second latch component 78m could alternatively be attached to the prosthetic blade 12.

The first latch component 76m includes a cage 170 including an opening 172 and a pair of spring members 174 disposed therein. The second latch component 76m includes a latch element 86m having a shape that approximates a shape of the opening 172.

The first latch component 76m may be positioned relative to the rail 32 such that when the second component 28 is moved the predetermined distance relative to the first component 26 and the distal end 16 of the prosthetic blade 12 engages the stop surface 58, the second latch component 78m is received by the cage 170. Specifically, the latch element 78m is positioned above the opening 172 and exerts a force on the spring members 174, thereby causing the spring members 174 to move away from one another. Once fully seated, the latch element 78m is retained within the opening 172 by the spring members 174 acting on the latch element 78m in a direction toward one another. At this point, a position of the second latch component 78m relative to the first latch component 76m is fixed.

The second latch component 78*m* may be removed from the first latch component 76*m* by moving the second latch component 78*m*—along with the second component 28 and sole structure 30—in a direction away from the first latch component 76*m* to allow the latch element 78*m* to disengage the spring members 174 and be removed from the opening 172. Removing the second latch component 78*m* from the first latch component 76*m* allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30*a*, 30*b*, 30*c*.

With reference to FIGS. 19A-19C, another latch mechanism 74*n* for use with the attachment system 10 is provided. In view of the substantial similarity in structure and function of the components associated with the latch mechanism 74 with respect to the latch mechanism 74*n*, like reference numerals are used hereinafter and in the drawings to identify like components while like reference numerals containing letter extensions are used to identify those components that have been modified.

The latch mechanism 74*n* includes a first latch component 76*n* attached to the prosthetic blade 12 and a second latch component 78*n* attached to the second component 28. While the first latch component 76*n* is shown and described as being attached to the prosthetic blade 12 and the second latch component 78*n* is shown and described as being attached to the second component 28, the first latch component 76*n* could alternatively be attached to the second component 28 and the second latch component 78*n* could alternatively be attached to the prosthetic blade 12.

The first latch component 76*n* includes a recess 176 having a post 178 disposed therein. In one configuration, the post 178 includes a ball 180 disposed at a distal end thereof. The second latch component 78*n* includes a pair of engagement blocks 182 biased toward one another by a pair of biasing members 184. In one configuration, the biasing members 184 are coil springs.

The first latch component 76*n* may be positioned relative to the rail 32 such that when the second component 28 is moved the predetermined distance relative to the first component 26 and the distal end 16 of the prosthetic blade 12 engages the stop surface 58, the second latch component 78*n* is received by the recess 176. Specifically, the ball 180 engages the engagement blocks 182, thereby causing the engagement blocks 182 to move away from one another against the bias of the biasing members 184. The engagement blocks 182 may each include a depression 186 sized to mate with the outer perimeter of the ball 180. As such, engagement between the engagement blocks 182 and the ball 180 maintains the second latch component 78*n* in contact with the first latch component 76*n*. At this point, a position of the second latch component 78*n* relative to the first latch component 76*n* is fixed.

The second latch component 78*n* may be removed from the first latch component 76*n* by moving the second latch component 78*n*—along with the second component 28 and sole structure 30—in a direction away from the first latch component 76*n* to allow engagement blocks 182 to disengage the ball 180 and be removed from the opening recess 176. Removing the second latch component 78*n* from the first latch component 76*n* allows the channel 46 to move relative to and along the rail 32. Sufficient movement of the channel 46 relative to and along the rail 32 allows the channel 46 to disengage the rail 32. Once disengaged from the channel 46, the rail 32 may be attached to another of the sole structures 30, 30*a*, 30*b*, 30*c*.

The following Clauses provide an exemplary configuration for an attachment system for securing to a prosthetic device, as described above.

Clause 1: An attachment system for use with a prosthetic device, the attachment system comprising a first component including a first surface, and further including one of a channel and a projection disposed on an opposite side of the first component than the first surface and a second component including a second surface, and further including the other of the channel and the projection disposed on an opposite side of the second component than the second surface, the other of the channel and the projection slidably engaging the one of the channel and the projection to selectively couple the first component and the second component together. The first surface and the second surface is operable to be attached to the prosthetic device and the other of the first surface and the second surface is operable to be attached to a sole structure having a ground-engaging surface.

Clause 2: The attachment system of Clause 1, wherein the slidably engaging comprises the channel matingly receiving the projection therein.

Clause 3: The attachment system of any of the preceding clauses, wherein the projection includes a first portion that is disposed at a junction of the prosthetic device and the one of the first surface and the second surface, and a second portion that is spaced apart from the first portion and is received by the channel, a cross-section of the projection being wider at the second portion than at the first portion.

Clause 4: The attachment system of Clause 3, wherein the channel and the projection cooperate to selectively provide a dovetail connection between the first component and the second component.

Clause 5: The attachment system of any of the preceding clauses, wherein the sole structure includes a cushioning layer disposed between the other of the first surface and the second surface and the ground-engaging surface.

Clause 6: The attachment system of Clause 5, wherein the ground-engaging surface is formed by the cushioning layer.

Clause 7: The attachment system of Clause 5, wherein the ground-engaging surface is formed by an outsole layer that is attached to the cushioning layer.

Clause 8: The attachment system of any of the preceding clauses, further comprising a latch mechanism operable to fix a relative position between the first component and the second component.

Clause 9: The attachment system of Clause 8, wherein the latch mechanism is automatically moved into a latched state to fix the relative position between the first component and the second component when the projection is moved into the channel a predetermined distance.

Clause 10: The attachment system of Clause 9, wherein the latch mechanism includes a male component that is fixed for movement with one of the first component and the second component and a female component that is fixed for movement with the other of the first component and the second component, the female component receiving the male component and securing the male component to the female component when the projection is moved the predetermined distance into the channel.

Clause 11: The attachment system of Clause 8, wherein the latch mechanism includes a latching element fixed for movement with one of the first component and the second component, and further including a latching feature fixed for movement with the other of the first component and the second component, the latching element operable to be actuated by and to engage the latching feature in response to a sliding engagement between the first component and the second component.

Clause 12: The attachment system of Clause 11, wherein the other of the first component and the second component includes a ramping surface operable to deflect the latching element to position the latching element into engagement with the latching feature.

Clause 13: The attachment system of any of the preceding clauses, wherein the prosthetic device is a foot prosthetic device.

Clause 14: The attachment system of Clause 13, wherein the prosthetic device is a blade prosthetic device.

Clause 15: The attachment system of any of the preceding clauses, wherein the first component and the second component are elongate components.

Clause 16: An attachment system for use with a prosthetic device, the attachment system comprising a first elongate component attached to the prosthetic device and a second elongate component attached to a sole structure having a ground-engaging surface, the second elongate component slidably receiving the first elongate component to attach the sole structure to the prosthetic device.

Clause 17: The attachment system of Clause 16, wherein the second elongate component matingly receives the first elongate component therein.

Clause 18: The attachment system of any of the preceding clauses, wherein the first elongate component includes a projection extending from a surface of the prosthetic device, the projection including a first portion disposed at a junction of the projection and the surface of the prosthetic device and a second portion that is spaced apart from the first portion and is received by the second component.

Clause 19: The attachment system of Clause 18, wherein a cross-section of the projection is wider at the second portion than at the first portion.

Clause 20: The attachment system of Clause 19, wherein the second component includes a channel, the channel and the projection cooperating to selectively provide a dovetail connection between the first elongate component and the second elongate component.

Clause 21: The attachment system of any of the preceding clauses, wherein the sole structure includes a cushioning layer disposed between the second elongate component and the ground-engaging surface.

Clause 22: The attachment system of Clause 21, wherein the ground-engaging surface is formed by the cushioning layer.

Clause 23: The attachment system of Clause 21, wherein the ground-engaging surface is formed by an outsole layer that is attached to the cushioning layer.

Clause 24: The attachment system of any of the preceding clauses, further comprising a latch mechanism operable to selectively fix a relative position between the first elongate component and the second elongate component.

Clause 25: The attachment system of Clause 24, wherein the latch mechanism is automatically moved into a latched state to fix the relative position between the first elongate component and the second elongate component when the first elongate component is slidably moved into the second elongate component a predetermined distance.

Clause 26: The attachment system of Clause 25, wherein the latch mechanism includes a male component that is fixed for movement with one of the first elongate component and the second elongate component, and further includes a female component that is fixed for movement with the other of the first elongate component and the second elongate component, the female component receiving the male component and securing the male component to the female component when the first elongate component is moved the predetermined distance into the second elongate component.

Clause 27: The attachment system of Clause 24, wherein the latch mechanism includes a latching element fixed for movement with one of the first elongate component and the second elongate component and a latching feature fixed for movement with the other of the first elongate component and the second elongate component, the latching element operable to be moved relative to the one of the first elongate component and the second elongate component to engage the latching feature.

Clause 28: The attachment system of Clause 27, wherein the other of the first elongate component and the second elongate component includes a ramping surface operable to deflect the latching element and to position the latching element into engagement with the latching feature.

Clause 29: The attachment system of any of the preceding clauses, wherein the prosthetic device is a foot prosthetic device.

Clause 30: The attachment system of Clause 29, wherein the foot prosthetic device is a blade prosthetic device.

Clause 31: The attachment system of any of the preceding clauses, wherein the first elongate component is integrally formed with the prosthetic device.

Clause 32: An attachment system for a prosthetic device, the attachment system comprising a first component attached to the prosthetic device and including a first latch mechanism and a second component selectively attachable to the first component, the second component including a second latch mechanism and a ground-engaging surface, the second latch mechanism configured and disposed to latchingly engage with the first latch mechanism when the first component is moved a predetermined distance relative to the second component in a first direction.

Clause 33: The attachment system of Clause 32, wherein the second latch mechanism is disposed on an opposite side of the second component than the ground-engaging surface.

Clause 34: The attachment system of any of the preceding clauses, wherein second component is slidably attached to the first component.

Clause 35: The attachment system of any of the preceding clauses, wherein the first component includes one of a projection and a channel and the second component includes the other of the projection and the channel, the channel receiving the projection to guide movement of the first component relative to the second component.

Clause 36: The attachment system of Clause 35, wherein the projection is matingly received by the channel and is permitted to slide relative to and within the channel to permit movement of the first component relative to the second component in the first direction.

Clause 37: The attachment system of Clause 36, wherein the projection includes a first end that is attached to one of the first component and the second component and a second end that is spaced apart from the first end and is received by the channel of the other of the first component and the second component, the projection having a cross-section that increases in width from the first end to the second end to restrict removal of the projection from the channel.

Clause 38: The attachment system of any of the preceding clauses, wherein the second portion includes a cushioning layer disposed between the prosthetic device and the ground-engaging surface.

Clause 39: The attachment system of Clause 38, wherein the ground-engaging surface is formed by the cushioning layer.

Clause 40: The attachment system of Clause 38, wherein the ground-engaging surface is formed by an outsole layer that is attached to the cushioning layer.

Clause 41: The attachment system of any of the preceding clauses, wherein the first latch mechanism includes one of a male component and a female component that is fixed for movement with the first component and the second latch mechanism includes the other of the male component and the female component, the female component being fixed for movement with the second component and receiving the male component to secure the male component to the female component when the first component is moved the predetermined distance in the first direction.

Clause 42: An attachment system for a prosthetic device, the attachment system comprising a first component fixed for movement with the prosthetic device and a second component that matingly receives the first component and includes a ground-engaging surface, the second component being automatically secured to the first component when the first component is moved a predetermined distance relative to the second component in a first direction.

Clause 43: The attachment system of Clause 42, wherein the first component includes a first latch mechanism and the second component includes a second latch mechanism.

Clause 44: The attachment system of Clause 43, wherein the second latch mechanism engages the first latch mechanism when the first component is moved the predetermined distance relative to the second component in the first direction.

Clause 45: The attachment system of Clause 44, wherein the first latch mechanism includes one of a male component and a female component that is fixed for movement with the first component and the second latch mechanism includes the other of the male component and the female component, the female component being fixed for movement with the second component and receiving the male component to secure the male component to the female component when the first component is moved the predetermined distance in the first direction.

Clause 46: The attachment system of Clause 43, wherein the second latch mechanism is disposed on an opposite side of the second component than the ground-engaging surface.

Clause 47: The attachment system of any of the preceding clauses, wherein second component is slidably attached to the first component.

Clause 48: The attachment system of any of the preceding clauses, wherein the first component includes one of a projection and a channel and the second component includes the other of the projection and the channel, the channel receiving the projection to guide movement of the first component relative to the second component.

Clause 49: The attachment system of Clause 48, wherein the projection is matingly received by the channel and is permitted to slide relative to and within the channel to permit movement of the first component relative to the second component in the first direction.

Clause 51: The attachment system of Clause 49, wherein the projection includes a first end that is attached to one of the first component and the second component and a second end that is spaced apart from the first end and is received by the channel of the other of the first component and the second component, the projection having a cross-section that increases in width from the first end to the second end to restrict removal of the projection from the channel.

Clause 52: The attachment system of any of the preceding clauses, wherein the second portion includes a cushioning layer, the cushioning layer disposed between the prosthetic device and the ground-engaging surface.

Clause 53: The attachment system of Clause 52, wherein the ground-engaging surface is formed by the cushioning layer.

Clause 54: The attachment system of Clause 52, wherein the ground-engaging surface is formed by an outsole layer that is attached to the cushioning layer.

The foregoing description has been provided for purposes of illustration and description. It is not intended to be exhaustive or to limit the disclosure. Individual elements or features of a particular configuration are generally not limited to that particular configuration, but, where applicable, are interchangeable and can be used in a selected configuration, even if not specifically shown or described. The same may also be varied in many ways. Such variations are not to be regarded as a departure from the disclosure, and all such modifications are intended to be included within the scope of the disclosure.

The invention claimed is:

1. An attachment system for use with a prosthetic leg, the attachment system comprising:
   a blade extending from a distal end to a proximal end along a first longitudinal axis and including (a) a first surface, (b) a second surface formed on an opposite side of the blade from the first surface and having a convex shape along a direction of the first longitudinal axis, (c) a first component comprising one of a channel and a projection disposed on the second surface and extending continuously along the direction of the first longitudinal axis from a first end at the distal end of the blade to a second end between the distal end and the proximal end, the first component having the convex shape of the second surface along the direction of the first longitudinal axis from the first end to the second end; and (d) a first latch component disposed on the second surface adjacent to the second end of the first component and aligned with the first component along the first longitudinal axis; and
   a sole structure extending from a third end to a fourth end along a second longitudinal axis and including (a) a ground-contacting surface, (b) an upper surface formed on an opposite side of the sole structure from the ground-contacting surface and having a concave shape along a direction of the second longitudinal axis, (c) a second component comprising the other of the channel and the projection formed on the upper surface and extending continuously from the third end to the fourth end along the direction of the second longitudinal axis, the second component having the concave shape of the upper surface along the direction of the second longitudinal axis and slideably engaging the first component along the direction of the first longitudinal axis to selectively couple the blade and the sole structure together, and (d) a second latch component disposed at the fourth end and aligned with the second component along the second longitudinal axis, the second latch component selectively engaging the first latch component of the blade.

2. The attachment system of claim 1, wherein the channel matingly receives the projection therein.

3. The attachment system of claim 1, wherein the projection extends outwardly from the second surface of the blade to a fifth end that is spaced apart from the second surface, and has a greater width at the fifth end than at the second surface.

4. The attachment system of claim 1, wherein the channel and the projection cooperate to selectively provide a dovetail connection disposed between the blade and the sole structure.

5. The attachment system of claim 1, wherein the sole structure includes a cushioning layer disposed between the upper surface and the ground-contacting surface.

6. The attachment system of claim 5, wherein the ground-contacting surface is defined by the cushioning layer.

7. The attachment system of claim 5, wherein the ground-contacting surface is defined by an outsole layer that is attached to the cushioning layer.

8. The attachment system of claim 1, wherein the first latch component and the second latch component are operable to fix a relative position between the blade and the sole structure.

9. The attachment system of claim 8, wherein the first latch component and the second latch component are automatically moved into a latched state to fix the relative position between the blade and the sole structure when the projection is moved into the channel a predetermined distance.

10. An attachment system for use with a prosthetic leg, the attachment system comprising:
a sole structure having a ground-contacting surface and a concave upper surface formed on an opposite side of the sole structure from the ground-contacting surface, a first elongate component extending continuously along the concave upper surface from a first end of the sole structure to a second end of the sole structure and defining a first longitudinal axis, and a first latch component disposed at the second end of the sole structure and aligned with the first longitudinal axis; and
a blade having a first surface facing in an opposite direction from the ground-contacting surface and a convex second surface formed on an opposite side of the blade from the first surface and facing the sole structure, the blade including (i) a second elongate component extending continuously along the convex second surface from a third end at a distal end of the blade to a fourth end in an intermediate portion of the blade and defining a second longitudinal axis and (ii) a second latch component disposed on the second surface of the blade adjacent to the fourth end of the second elongate component and aligned with the second longitudinal axis, the first elongate component slideably received by the second elongate component between the sole structure and the blade to engage the first latching component with the second latching component.

11. The attachment system of claim 10, wherein the second elongate component is a projection that extends outwardly from the second surface of the blade to a fifth end that is spaced apart from the second surface and has a greater width at the fifth end than at the second surface.

12. The attachment system of claim 10, wherein the first elongate component and the second elongate component cooperate to selectively provide a dovetail connection between the first elongate component and the second elongate component.

13. The attachment system of claim 10, wherein the sole structure includes a cushioning layer disposed between the second elongate component and the ground-contacting surface.

14. The attachment system of claim 13, wherein the ground-contacting surface is defined by the cushioning layer.

15. The attachment system of claim 13, wherein the ground-contacting surface is formed by an outsole layer that is attached to the cushioning layer.

16. The attachment system of claim 10, wherein the first latch component and the second latch component are operable to selectively fix a relative position between the first elongate component and the second elongate component.

17. The attachment system of claim 16, wherein the first latch component and the second latch component are automatically moved into a latched state to fix the relative position between the first elongate component and the second elongate component when the projection is slideably received in the channel a predetermined distance.

* * * * *